United States Patent [19]

Rostoker et al.

[11] Patent Number: 4,829,152
[45] Date of Patent: May 9, 1989

[54] METHOD OF RESISTANCE WELDING A POROUS BODY TO A SUBSTRATE

[75] Inventors: William Rostoker; Julius J. Bonini; Arne R. Jarnholm, all of Chicago, Ill.

[73] Assignee: Rostoker, Inc., Burnham, Ill.

[21] Appl. No.: 120,927

[22] Filed: Nov. 16, 1987

[51] Int. Cl.$^4$ ............................................. B23K 11/00
[52] U.S. Cl. ................................ 219/78.02; 219/117.1
[58] Field of Search ................... 219/78.02, 117.1, 118; 228/173.1, 173.2, 173.3, 178

[56] References Cited

U.S. PATENT DOCUMENTS

| | | | |
|---|---|---|---|
| 2,866,886 | 12/1958 | Koehring | 219/117 |
| 3,605,123 | 9/1971 | Hahn | 3/1 |
| 3,789,498 | 2/1974 | Cole | 29/470.9 |
| 3,852,045 | 12/1974 | Wheeler et al. | 29/182 |
| 3,905,777 | 9/1975 | Lacroix | 29/183.5 |
| 3,906,550 | 9/1977 | Rostoker et al. | 3/1.912 |
| 4,038,703 | 8/1977 | Bokros | 3/1.5 |
| 4,064,567 | 12/1977 | Burstein et al. | 3/1.91 |
| 4,205,400 | 6/1980 | Shen et al. | 3/1.91 |
| 4,406,023 | 9/1983 | Harris | 3/1.912 |
| 4,478,904 | 10/1984 | Ducheyne et al. | 428/288 |
| 4,479,271 | 10/1984 | Bolesky et al. | 3/1.913 |
| 4,495,664 | 1/1985 | Blanquaert | 3/1.913 |
| 4,547,694 | 10/1985 | Himmelbauer | 313/384 |
| 4,570,271 | 2/1986 | Sump | 623/18 |
| 4,660,755 | 4/1987 | Farling et al. | 228/178 |

FOREIGN PATENT DOCUMENTS 2142544A 1/1985 United Kingdom .

OTHER PUBLICATIONS

Sales Brochure from Filter Products Division, Facet Enterprises, Inc. 434 W. 12 Mile Road, Madison Heights, Mich. 48071.

Smithells, C. J., *Tungsten*, Chemical Publishing Co., N.Y., N.Y. (1953), pp. 94–100.

Kingston, W. E., *The Physics of Powder Metallurgy*, McGraw-Hill, N.Y., N.Y. (1951) pp. 263–277.

Wulff, Jr. *Powder Metallurgy*, ASM, Cleveland, Ohio, 1940, 1942 pp. 423–430, 590, 591.

Hara, Z. et al. Electrical Resistance-Sintering of Titanium Metal, Alloys and Composites, (see Supp. Info. Disc. State.).

Ducheyne, P. et al. Titanium Implants with Porous Structures for Bone Ingrowth: A General Approach (see Supp. Info. Disc. State.).

*Primary Examiner*—E. A. Goldberg
*Assistant Examiner*—Lincoln Donovan
*Attorney, Agent, or Firm*—Arne R. Jarnholm

[57] ABSTRACT

A method for resistance welding a metallic porous body, comprised of a plurality of metallic components arranged in a three dimensional matrix so as to have interconnecting pores or voids formed between said components, to a metallic substrate. The porous body and substrate each define a faying surface. The porous body is impregnated with an electrically conductive material to a predetermined distance from its faying surface, thereby defining an impregnated zone and an unimpregnated zone. The faying surfaces of the substrate and porous body are brought into physical contact so that the unimpregnated zone is disposed between the impregnated zone and faying surface of the porous body. An electrical current is passed through the porous body and the substrate, across the faying surfaces thereby forming a metallurgical bond between the faying surfaces. In the preferred embodiment of the invention: the porous body and substrate are forcibly pressed together, during the step of passing said electrical current; the unimpregnated zone is densified; and a forge weld is formed between the components of the porous body at the faying surface of the porous body and the faying surface of the substate. The electrically conductive impregnating material is preferably a metal or alloy and works to increase the electrical conductance of the impregnated zone and to preserve the porosity of the porous body in the impregnated zone.

24 Claims, 11 Drawing Sheets

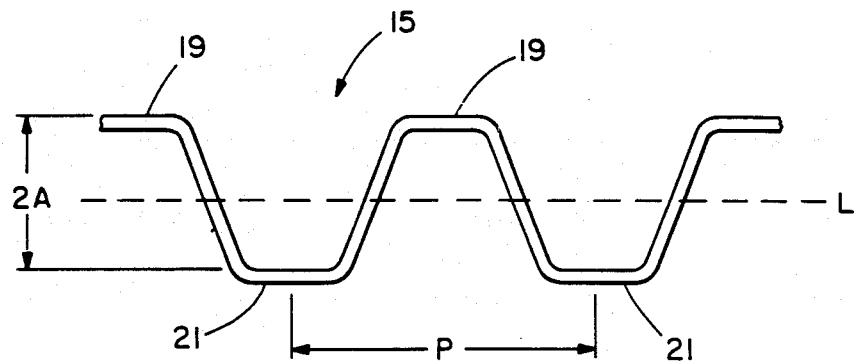
FIG. 2
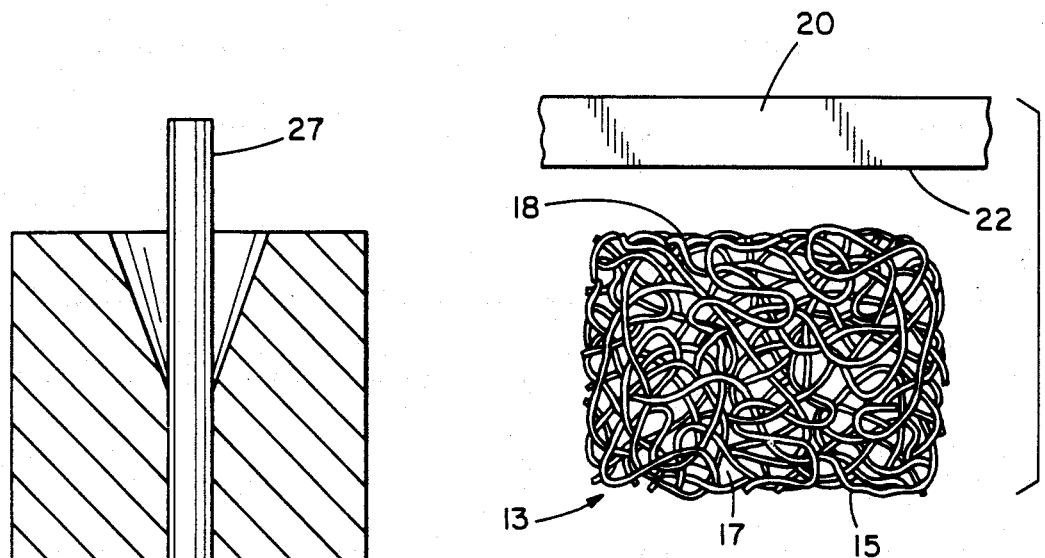
FIG. 3
FIG. 1
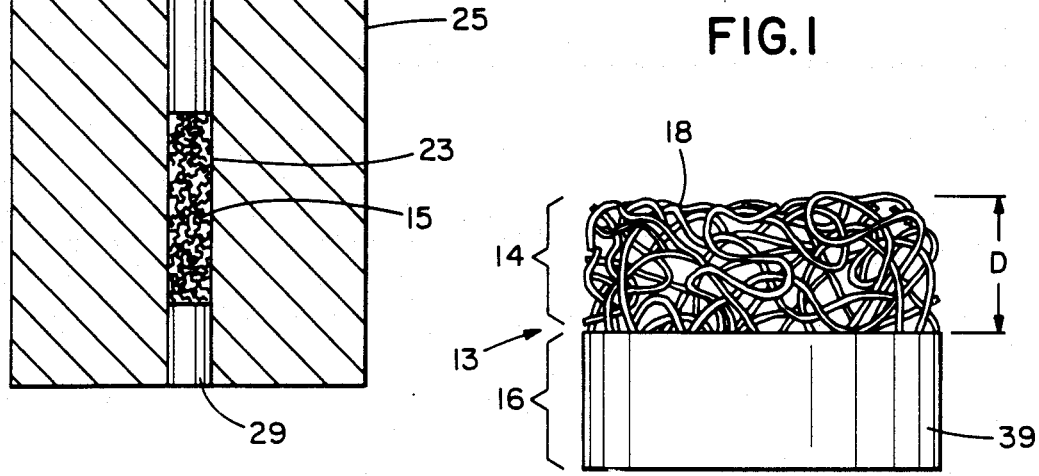
FIG. 4

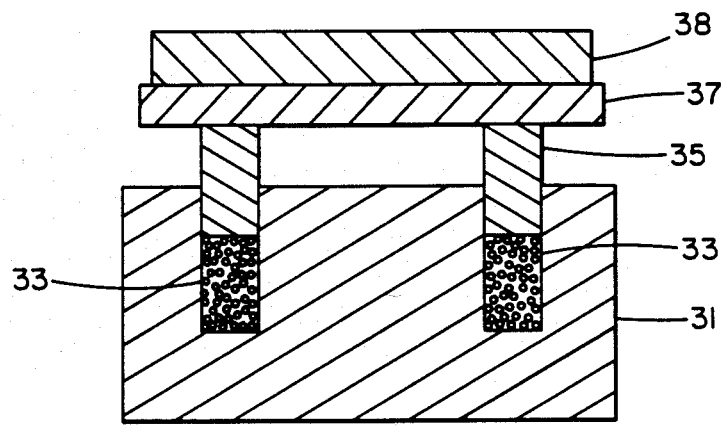
FIG. 6
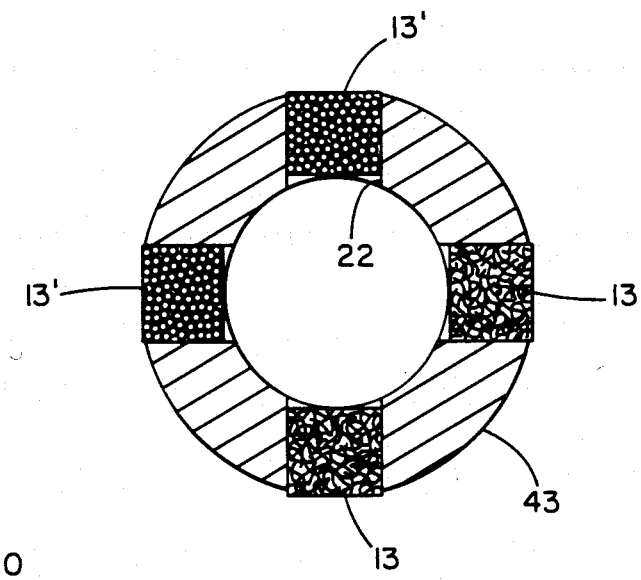
FIG. 9
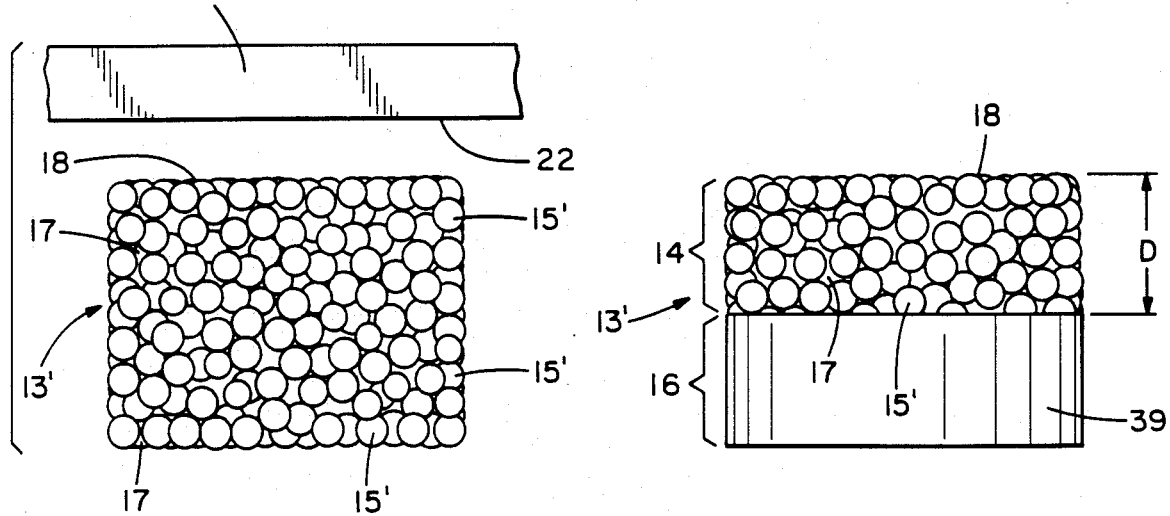
FIG. 5
FIG. 7

MAGNIFICATION - 6X

MAGNIFICATION - 400X

MAGNIFICATION - 400X

MAGNIFICATION – 6X

MAGNIFICATION – 400X

MAGNIFICATION – 400X

MAGNIFICATION-6X

MAGNIFICATION-400X 14,000 PSI
MAGNIFICATION-20X 7,000 PSI
MAGNIFICATION-20X 3,500 PSI
MAGNIFICATION-20X

MAGNIFICATION—6X

MAGNIFICATION—750X

MAGNIFICATION—40X

MAGNIFICATION - 400X

MAGNIFICATION - 400X

MAGNIFICATION - 400X

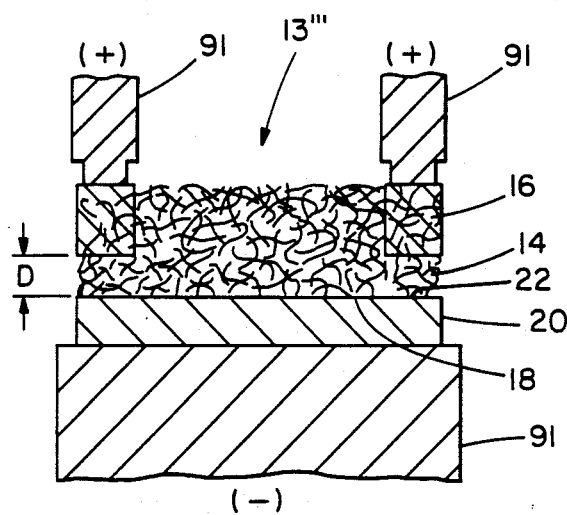
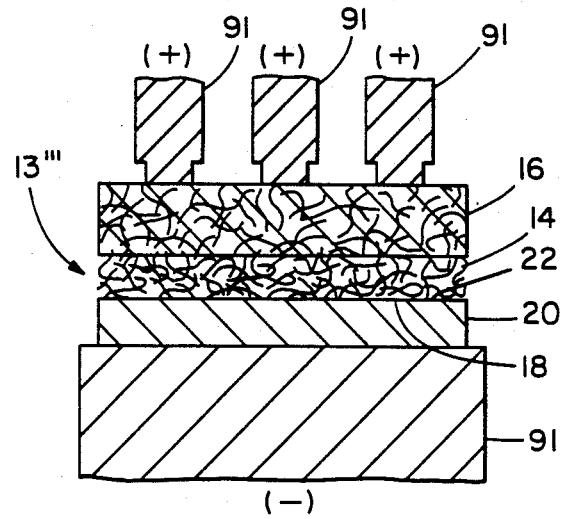
FIG. 28    FIG. 29
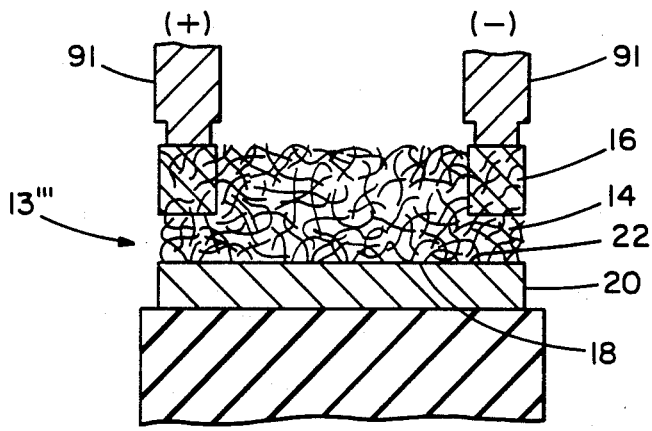
FIG. 30
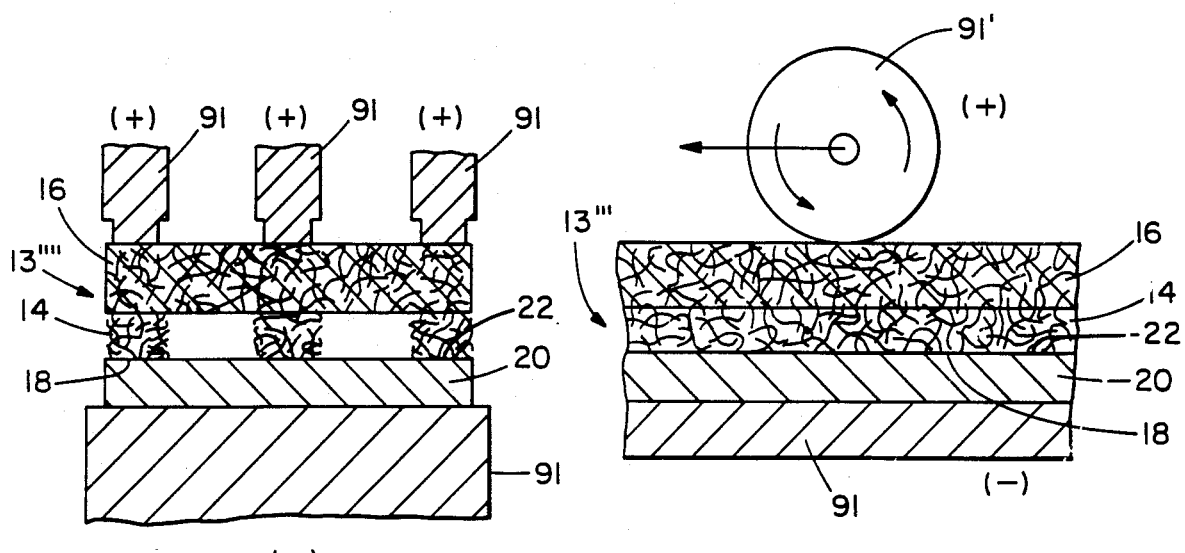
FIG. 31    FIG. 32

METHOD OF RESISTANCE WELDING A POROUS BODY TO A SUBSTRATE

FIELD OF THE INVENTION

The present invention relates generally to the field of metallurgy and more specifically to a method for welding a porous body to a substrate.

DESCRIPTION OF THE PRIOR ART

In many areas of manufacture, it is necessary or desirable to bond a porous body to the surface of a substrate. For instance, journal bearings in the yoke of universal joints are often a powder metal part, having intentionally retained porosity for the purpose of holding lubricant. Another example of such bonding is in the manufacture of fluid filters, wherein the filters are fabricated from wire mesh. Such filters are often bonded to the interior walls of conduit which carries the fluid stream. Perhaps the most notable area of manufacture which employs the joinder of a metallic, porous body to a substrate, is in the field of orthopedic prosthetic devices. A porous body on the surface of a load-bearing member in a prosthetic device allows for bony ingrowth and tissue invasion, thereby anchoring the prosthetic device in the patient without the use of adhesive.

As used herein, the term "substrate" simply means a metallic member to which the aforementioned porous body is joined. Thus, the porous bodies and substrates described herein each define a faying surface (i.e. the surfaces between which a bond is ultimately formed). In most instances, the substrate is substantially solid, that is a member having no intentionally introduced porosity. Such is clearly the case with prosthetic devices wherein the load-bearing member comprises a metal casting. The castings may contain shrinkage porosity, which is highly undesirable as it compromises strength and fatigue life. In general, the term "substrates" also includes forgings, sheet, plate, bar and milled and machined metal shapes and sections. While it is believed that the method of the present invention will find the most utility in the joinder of porous bodies to substantially solid substrates, it will become clear to one skilled in the art that the invention is not so limited.

Also as used herein, the terms "metallic porous body" or simply "porous body" mean a body comprising a plurality of metal components, arranged in a three dimensional matrix so as to form interconnecting pores, or voids, between the metal components. The shape of the components is variable and can range from highly defined geometries, such a spheres or filaments, to somewhat irregular shapes, such as ligaments and dendritic configurations, and even to completely amorphous shapes.

The components in a porous body may or may not be bonded together. In the case of unbonded metal beads or powders, the porous body assumes the shape of its container. In the case of a porous body formed from wire, mechanical bonding may be achieved by interlocking of the individual filaments. The components can also be bonded together by another material, such as an adhesive, solder or brazing material. Finally, the individual components may be bonded together by metallurgical bonds formed at the areas of contact between the components and rendering a structure wherein the components are contiguous with one another. Such is the case when a metallic porous body is subjected to a sintering treatment, at temperatures and for a time appropriate for the given metal or alloy. Such is also the case when the components of the porous body comprise contiguous ligaments, as in the case of titanium sponge.

A number of materials, including ceramics, have been used to construct prosthetic devices and porous bodies associated therewith. The large majority, however, are fabricated from biocompatible metals and their alloys, the primary ones being unalloyed titanium, 90% titanium - 6% aluminum - 4% vanadium, and 65% cobalt - 30% chromium - 5% molybdenum.

In U.S. Pat. No. 3,906,550, Rostoker, et al., there is disclosed the use of cut lengths of sinusoidally kinked wire, molded and metallurgically bonded together to form a porous fiber metal body. The prosthetic device of Rostoker, et al. may be entirely constructed from the porous fiber metal material or, as in the case of most prosthetic devices, may include a substantially solid, load-bearing member. In the latter instance, the porous fiber metal body must be securely bonded to the solid member, or substrate, to permit the transfer of loads thereto. Attachment of the porous body to the substrate, and metallurgical bonding between the individual wire filaments, can be simultaneously accomplished by sintering at a temperature appropriate for the given alloy.

Another type of porous body for orthopedic prostheses, currently in wide use, is fabricated from relatively coarse metal powders or metal beads. To maximize porosity, the particle size of the beads or powders is preferably uniform. Particle size also determines the size of the pores or voids formed, which must be matched to the optimum pore size which promotes bony ingrowth. For human bone prostheses, beads or powders between about $-30$ to $+45$ Tyler mesh are often used. The beads or powders are frequently sintered in situ, which causes metallurgical bonding between the individual particles and the porous body and the prosthesis substrate.

Sintering, to obtain bonding between a porous body and a substrate, has several drawbacks. The mechanical properties of many metals, especially titanium and its alloys, are adversely affected by exposure to atmospheric gases at sintering temperatures. Thus, sintering must be carried out in specially constructed furnaces that are capable of maintaining extremely high vacuum or a high purity, inert atmosphere. The expense of purchasing, operating and maintaining such equipment represents a substantial portion of the cost of prosthetic devices.

The times and temperatures associated with reasonably high strength sintered bonds are also sufficient to cause substantial modifications in the microstructure of the porous body and the substrate, which may include grain growth and the precipitation of unwanted phases. Such microstructural modifications, especially in the loadbearing substrate member, can ultimately lead to catastrophic failure.

A further drawback to sintering, as a means of affixing a porous body to a substrate, results from the geometry of the porous materials. In the cases of porous bodies fabricated from kinked wires or beads, the true area of contact between the porous body and the solid substrate is extremely small. A truly spherical bead resting on a relatively flat surface theoretically produces only point contact. A truly cylindrical wire resting on a flat surface theoretically produces only line contact. In reality, point contact is also the principal mode of contact between a relatively flat surface and a fiber metal body, molded from kinked wires. Because a sintered bond requires solid state diffusion between the components being joined, a small area of contact results in a very small area of bonding.

Furthermore, the geometry of the bond obtained by conventional sintering is far from desirable. The point contact between the individual beads or wires and a solid substrate results in a bond that presents a notched condition. It is suspected that such a notched condition in prosthetic devices substantially reduces the fatigue life which could be obtained if the condition could be eliminated.

Previous attempts have been made to increase the area of bonding, as well as the number of bonds, by forcing the porous body against the substrate during the sintering operation. Heretofore, this has resulted in compaction of the porous body and loss of porosity, due to metal creep at sintering temperatures. Furthermore, the force can only be applied as a weight, resting on the porous body, as creep also will cause the loss of mechanical pressure applied by a clamp or screw which is subjected to sintering temperatures.

Finally, sintering is a less than ideal method for joining dissimilar metals or alloys. Because sintering relies on diffusion to obtain bonding, dissimilar metals joined thereby, alloy at the joint interface. In many cases this can result in the precipitation of brittle intermetallic compounds which can serve as a site for initiating a fatigue crack.

Brazing has also been used to affix a porous body to a solid substrate. By capillary action, the brazing metal tends to flow into the pores and thereby destroys the desired porosity. Furthermore, because brazing metals are molten they can and often do dissolve metal from the substrate and porous body. This can also result in the formation of brittle, intermetallic compounds as in the case of a low carbon, Co-Cr alloy substrate and porous body joined by a high carbon, lower melting, Co-Cr brazing compound. Finally, in the case of prosthetic devices, the brazing metal must also be biocompatible.

Another method of affixing a metallic, porous body to a substantially solid, metallic substrate, in the context of constructing an orthopedic prosthesis, is disclosed by Farling et al., in U.S. Pat. No. 4,660,755, assigned to Zimmer, Inc. of Warsaw, Ind. Farling et al. teach the use of an electrical current, passed through the porous body and substrate, to simultaneously obtain metallurgical bonding between the points of contact in the porous body and between the porous body and solid substrate. At the same time the electrodes are advanced to cause compaction of the porous body, presumably to the desire level of porosity. The time required to obtained bonding is reported to be between about 30 and 180 seconds.

The method of Farling et al. suffers from a number of drawbacks. First of all, the amount of pressure that can be applied by the electrodes is limited by the degree of compaction in the porous body that is considered tolerable. Secondly, electrode travel is limited by stops, which are independent of the porous layer. Thus, the pressure applied by the electrodes is quickly dissipated as the porous body heats to sintering or welding temperatures and the stresses created in the porous body are relieved by creep. Finally, the method of Farling et al. does not provide any means for increasing either the number of bonds or the areas of the bonds between the porous body and the solid substrate.

Thus, there has long existed a need for a method of affixing a metallic porous body to a metallic substrate, which process: prevents the loss of porosity during the joining process; produces minimal changes in the microstructure of the substrate; prevents detrimental alloying between the metallic porous body and substrate; increases the number of bonds between the porous body and substrate, as compared to sintering; increases the individual bond areas, also as compared to sintering; and provides bonds of a geometry that minimizes the severity of the notch presented.

BRIEF SUMMARY OF THE INVENTION

In accordance with the present invention, a metallic porous body is resistance welded to a metallic substrate. The porous body and the substrate each define a faying surface. The porous body comprises a plurality of metal components, arranged in a three dimensional matrix so as to form a plurality of interconnecting pores, or voids, between the components. A substantial number of the components are in electrical communication. The porous body is impregnated with an electrically conductive material to a predetermined distance from the faying surface, thus defining an impregnated and unimpregnated zone. The faying surfaces of the porous body and substrate are brought into contact and an electrical current is passed through the porous body and substrate, across the faying surfaces, to form a metallurgical bond therebetween. The electrically conductive impregnating material works to decrease the electrical resistance and increase the heat capacity of the impregnated zone. Thus, the unimpregnated zone preferentially heats to a higher temperature, and creates a weld, while the impregnated zone remains relatively cool.

In the preferred embodiment of the invention, the porous body and substrate are forge welded, that is to say welded together without melting either the porous body or substrate. In this embodiment, the porous body and substrate are forcibly pressed together, simultaneously with the step of passing the electrical current therethrough. It is important that the current density, and the duration of current application, be sufficiently great to heat the unimpregnated zone to its hot working temperature, yet be sufficiently low to prevent melting of the porous body, electrically conductive impregnating material or substrate. The force, or a component thereof, is applied in a direction normal to the faying surfaces. It is also preferred that the force, and the pressure created thereby, be of sufficient magnitude to cause: densification of the unimpregnated zone of the porous body by plastic deformation; metallurgical bonding between the individual components in the densified, unimpregnated zone; and metallurgical bonding between the components at the faying surface of the porous body and the faying surface of the substrate. The process of electrical resistance forge welding, as opposed to fusion welding, can be controlled so that no discernable alloying occurs between the porous body and the substrate. Thus, the microstructure of the substrate is free of substantial changes such as grain growth and the precipitation of unwanted phases.

In the electrical resistance forge welding process of the present invention, the electrically conductive impregnating material acts to bear the load in the impregnated zone. Thus, the unimpregnated zone is densified and the porosity in the impregnated zone remains unchanged during the forge welding process. Subsequent removal of the electrically conductive impregnating materials may be carried out by leaching, etching, evaporation, exudation or oxidation, thus leaving the porosity of the previously impregnated zone intact.

It is also preferred that the porous body and solid substrate are fabricated from metals or alloys having a relatively high melting point or solidus, such as titanium, Co-Cr alloys or stainless steel. The electrically conductive, impregnating material is preferably chosen to have a relatively low melting point or liquidus compared to that of the material comprising the porous body. When the porous body is fabricated from titanium or stainless steel, good choices for the impregnating material include calcium, magnesium and their alloys.

The electrically conductive impregnating metal or alloy is also preferably matched to the metal or alloy from which the porous body is fabricated so that very little, if any, dissolution or alloying of the porous body can result from contact with the impregnating material. Thus, the porous body may be impregnated by immersion in a molten pool of the electrically conductive material.

It is therefore an object of the present invention to provide a method of resistance welding a porous body to a substrate that increases the number of metallurgical bonds between the components of the porous body and the faying surface of the substrate, as compared to prior art methods of joining a porous body and substrate.

Another object of the present invention is to provide a method of resistance welding a porous body to a substrate that increases the total metallurgical bond area between the faying surfaces of the porous body and substrate, as compared to prior art methods of joining a porous body to a substrate.

Another object of the present invention is to provide a method of resistance welding a porous body to a substrate, wherein the bonds between the substrate and the components of the porous body do not present a notched condition.

Still another object of the present invention is to provide a method of resistance forge welding a porous body to a substrate wherein the porosity of a substantial portion the porous body remains unchanged.

Yet another object of the invention is to provide a method of joining a metallic porous body to a metallic substrate, wherein the porous body and substrate are fabricated from dissimilar metals or alloys and wherein there is no discernable diffusion or alloying between the porous body and substrate.

These and other objects and features of the invention will become apparent to those skilled in the art from the following detailed description and drawings and photomicrographs of which:

FIG. 1 is a front elevation of a porous body, fabricated from sinusoidally kinked titanium [grade I, commercially pure, 11 mil diameter] wire components, molded into the shape of a right cylinder having a diameter of about 0.25 inch and a height of about 0.20 inch (vacuum sintered for two hours at 1,200° C. after molding), the uppermost flat face of the cylinder defining a faying surface. Also included is a side view of a substantially solid substrate, in the form of a square coupon, about 0.75 by 0.75 inch on a side, cut from a sheet of Ti - 6Al - 4V alloy (annealed condition), about 0.125 thick;

FIG. 2 is a plan view of the sinusoidally kinked wire component used to mold the porous body shown in FIG. 1;

FIG. 3 is a front elevation, shown in partial cross section, of the die and ram used to mold the porous body shown in FIG. 1;

FIG. 4 is front elevation of the porous body shown in FIG. 1 been impregnated with an electrically conductive material to a predetermined distance from the faying surface.

FIG. 5 is a front elevation of another type of porous body, fabricated from grade II commercially pure titanium beads (−30 +45 Tyler mesh, also vacuum sintered for two hours at 1,200° C.) also in the shape of a right cylinder having overall dimensions about the same as the porous body shown in FIG. 1, the uppermost flat face of the cylinder defining a faying surface;

FIG. 6 is a side elevation, shown in cross section, of a mold assembly used to fabricate the porous body shown in FIG. 5;

FIG. 7 is a front elevation of the porous body shown in FIG. 5 which has been impregnated with an electrically conductive material to a predetermined distance from its faying surface;

FIG. 9 is a cross-sectional view of the fixture shown in FIG. 8 taken along the line 9—9;

FIGS. 11 through 27 are photomicrographs of porous bodies which have been affixed to substantially solid substrates. In each of these Figures, except FIGS. 18 and 24, the porous body was affixed to the substrate in accordance with the present invention. Each photomicrograph presents a view of a section taken in a plane substantially normal to the faying surfaces of the porous body and substrate. One half of the joined and sectioned porous body and substrate was mounted in either epoxy or phenolic mounting compound and ground and polished to the degree necessary to bring out the desired features of each photomicrograph. In each instance, the location of the view in the aforedescribed plane, the magnification of the photomicrograph (number of diameters hereinafter designated simply as "X") and, whether the sample is etched or unetched is indicated. The features of interest revealed by these photomicrographs are discussed below, in the Detailed Description Of The Invention.

Figure 11:
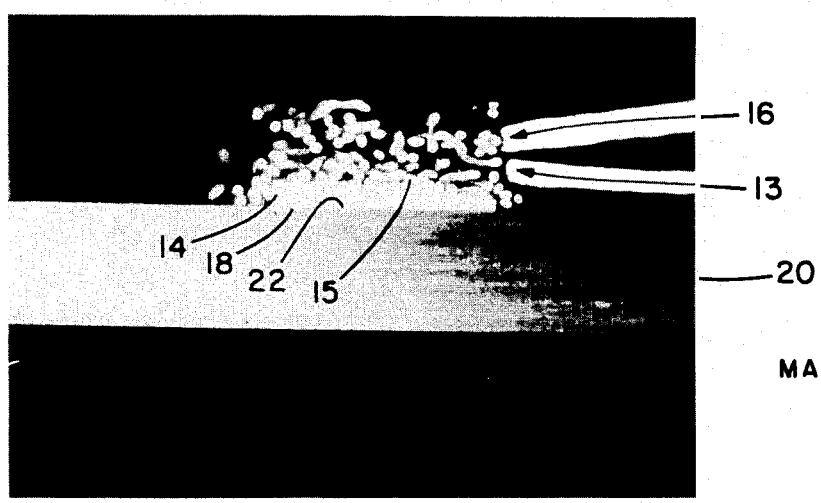
Figure 12:
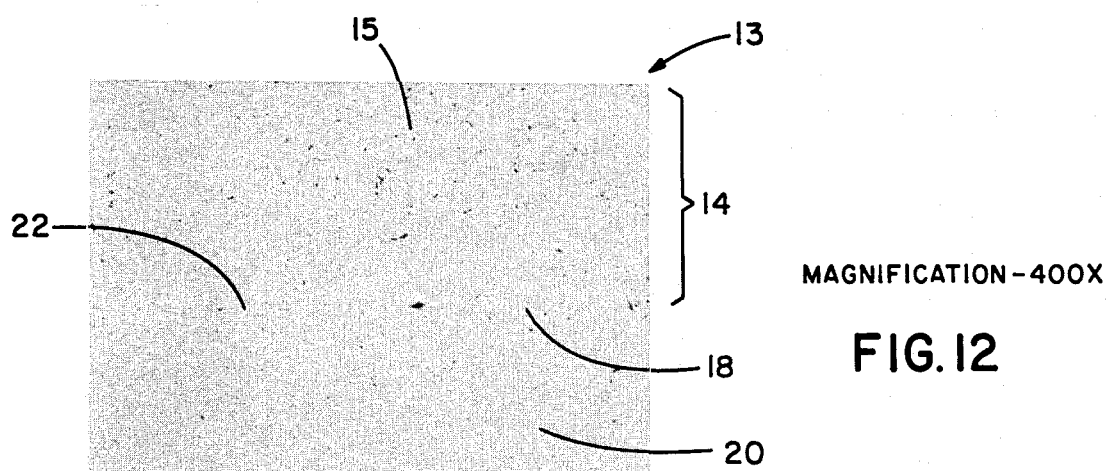
Figure 13:
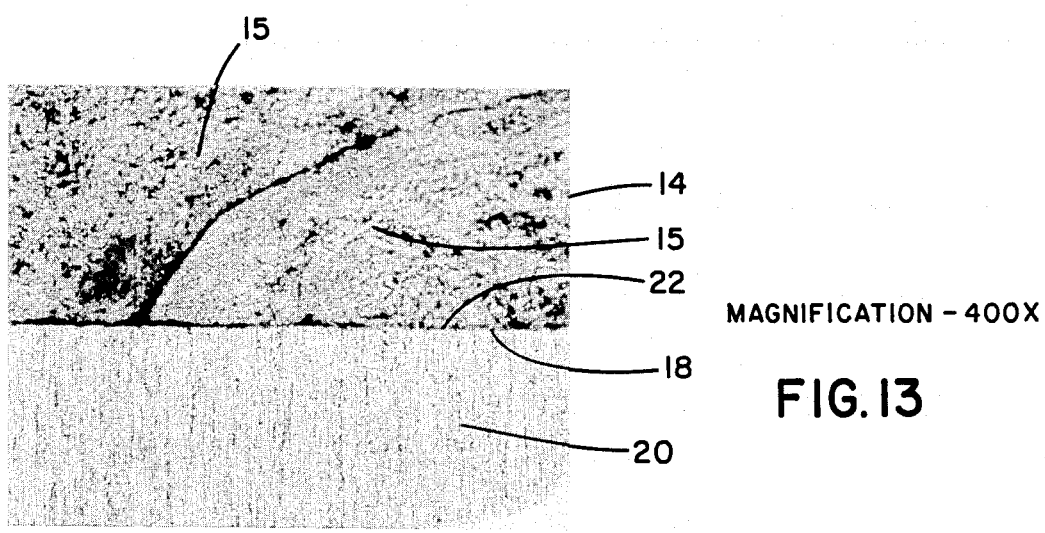
Figure 14:
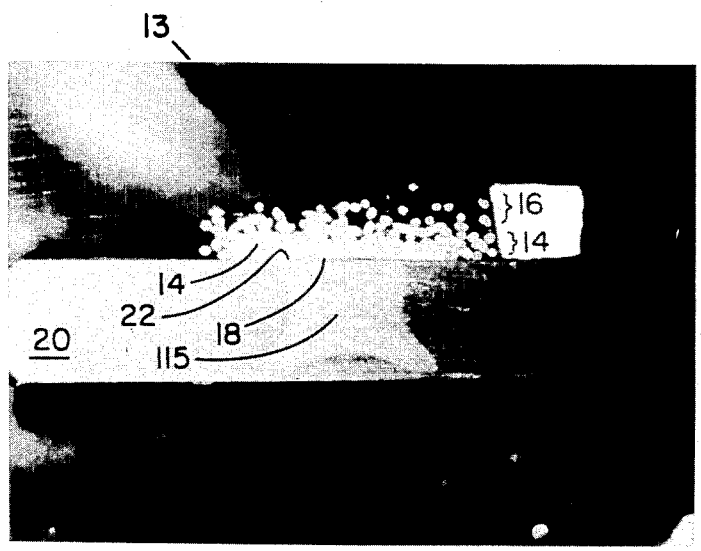
Figure 15:
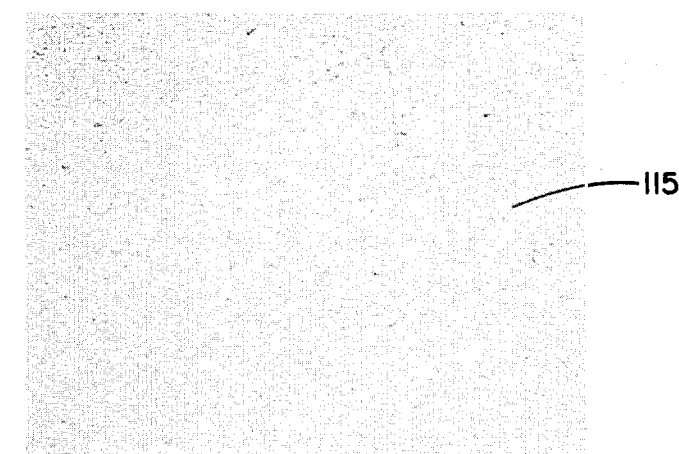
Figure 16:
Figure 17:
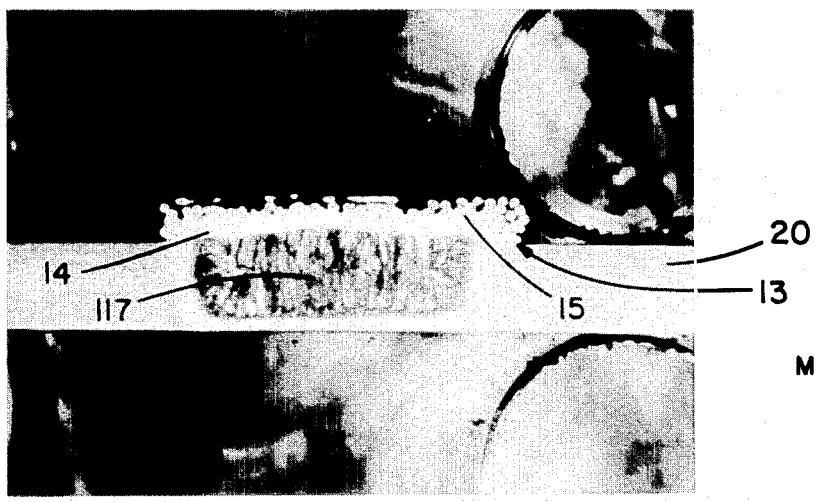
Figure 18:
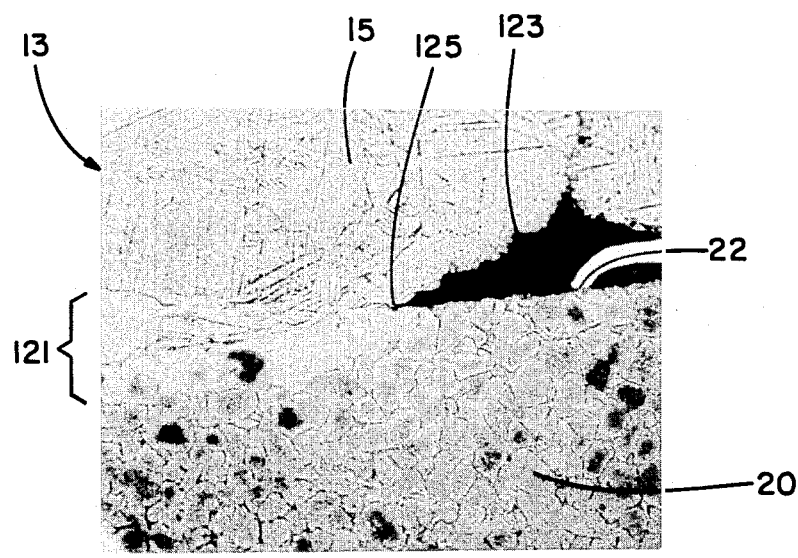
Figure 19:
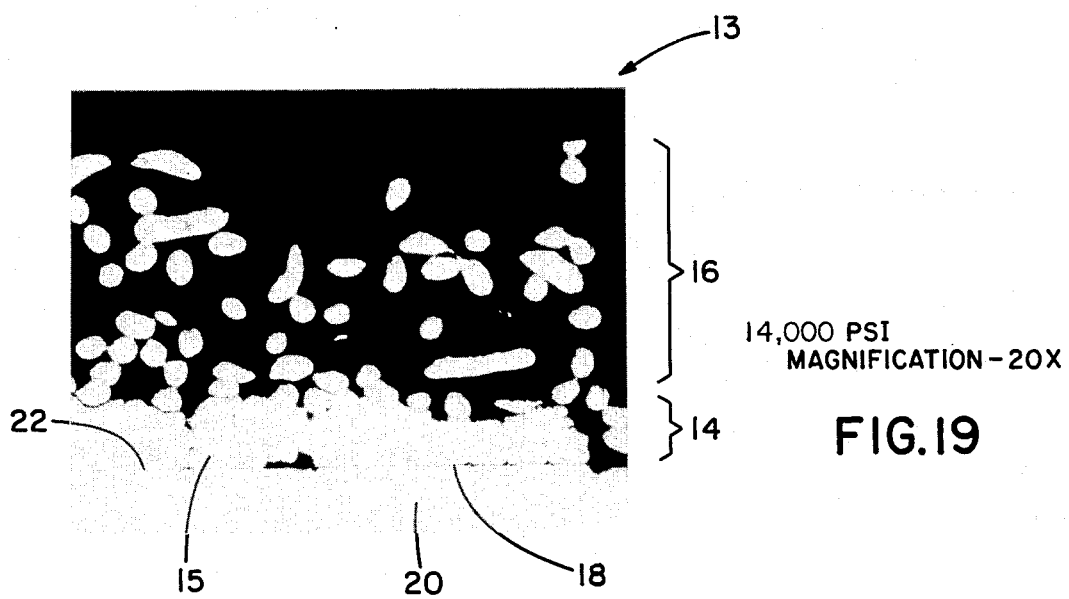
Figure 20:
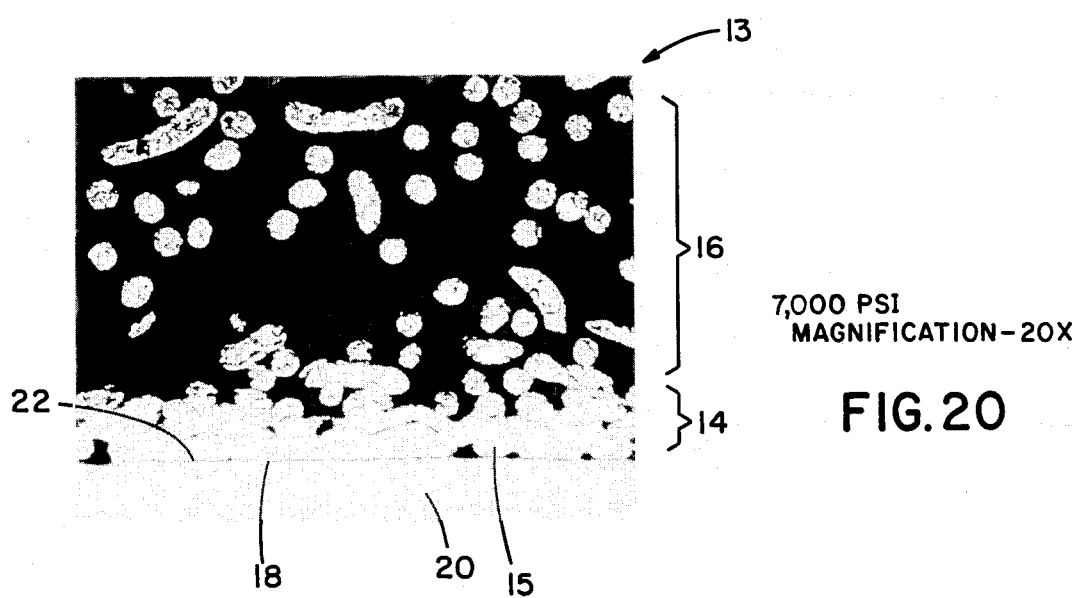
Figure 21:
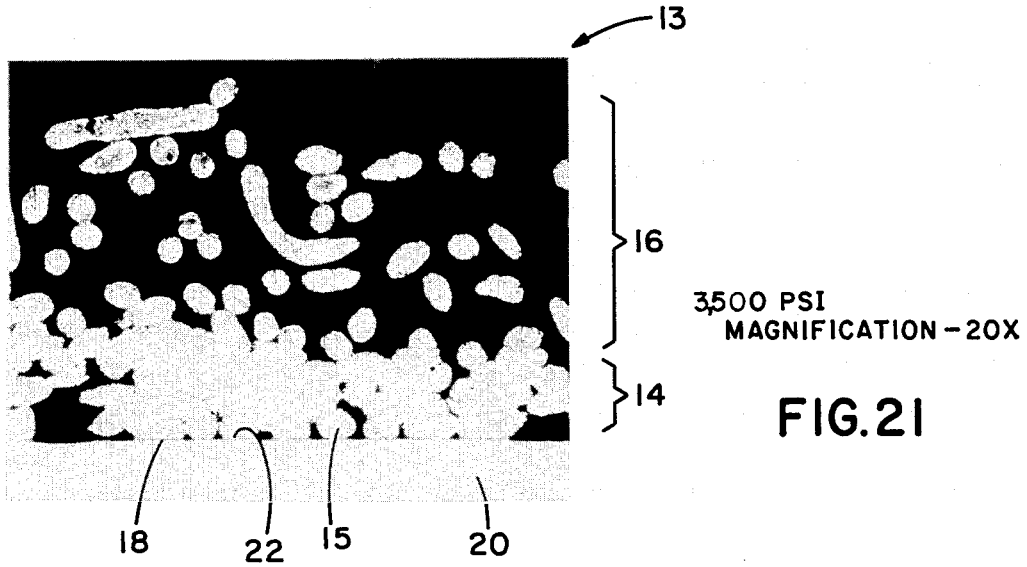
Figure 22:
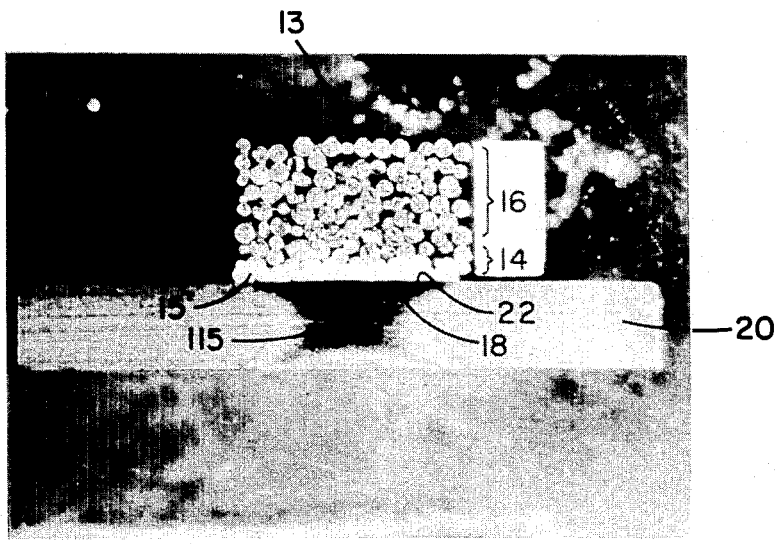
Figure 23:
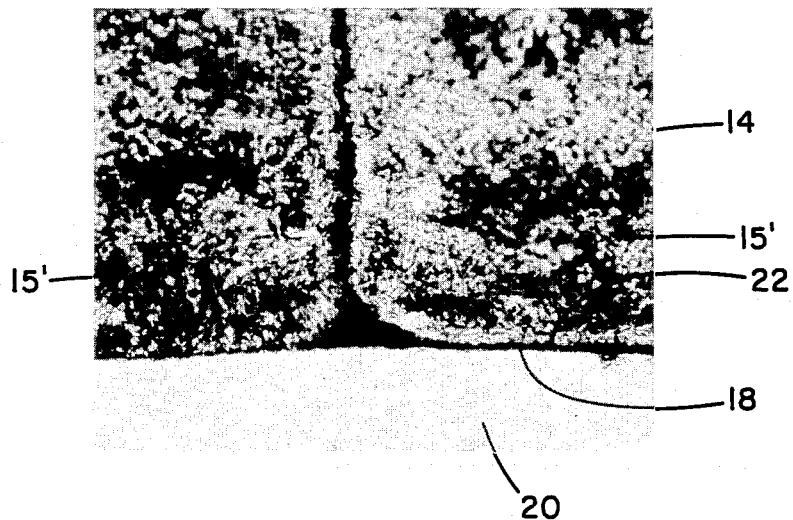
Figure 24:
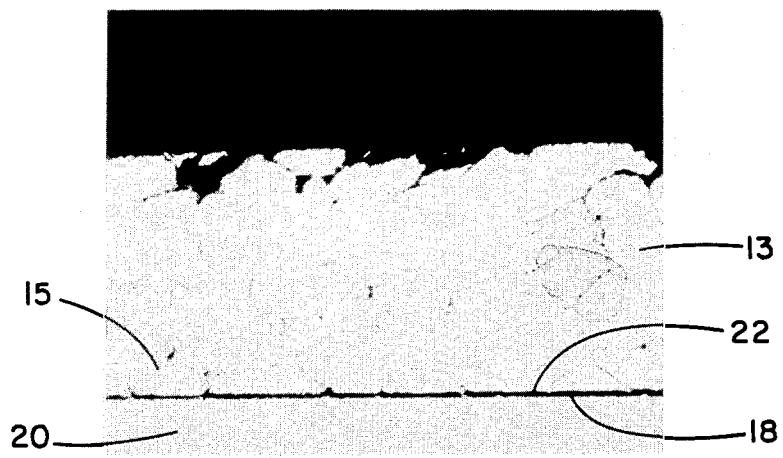
Figure 25:
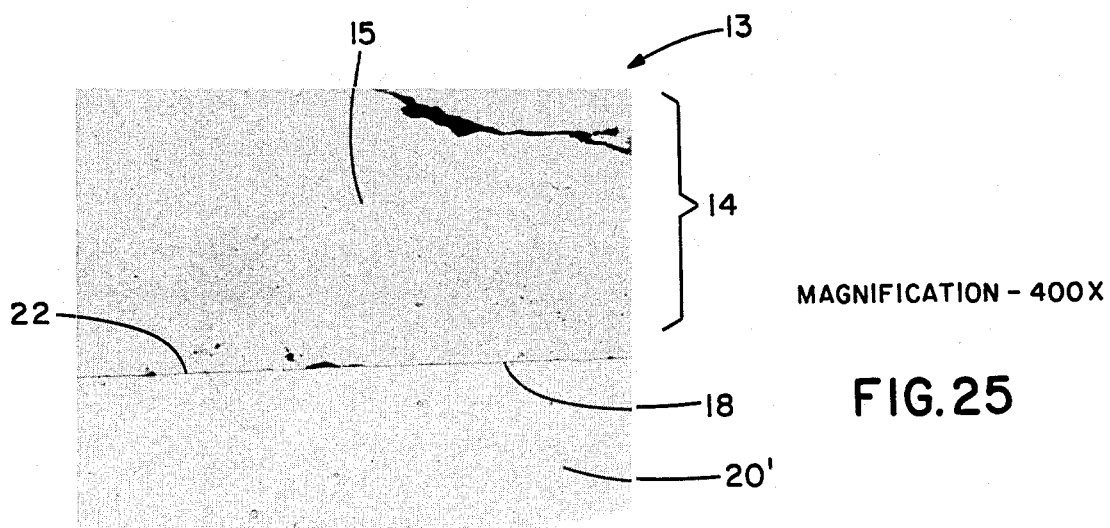
Figure 26:
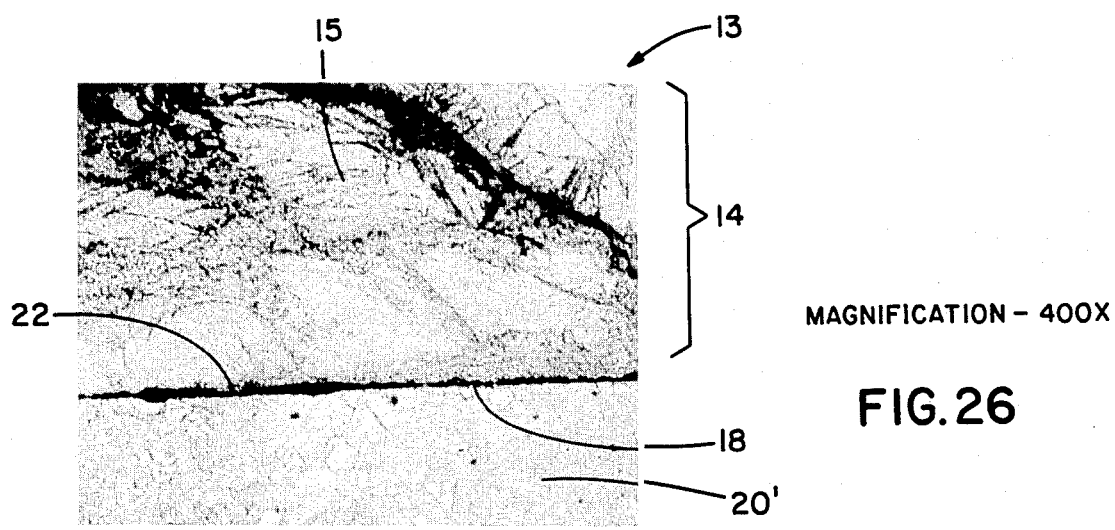
Figure 27:
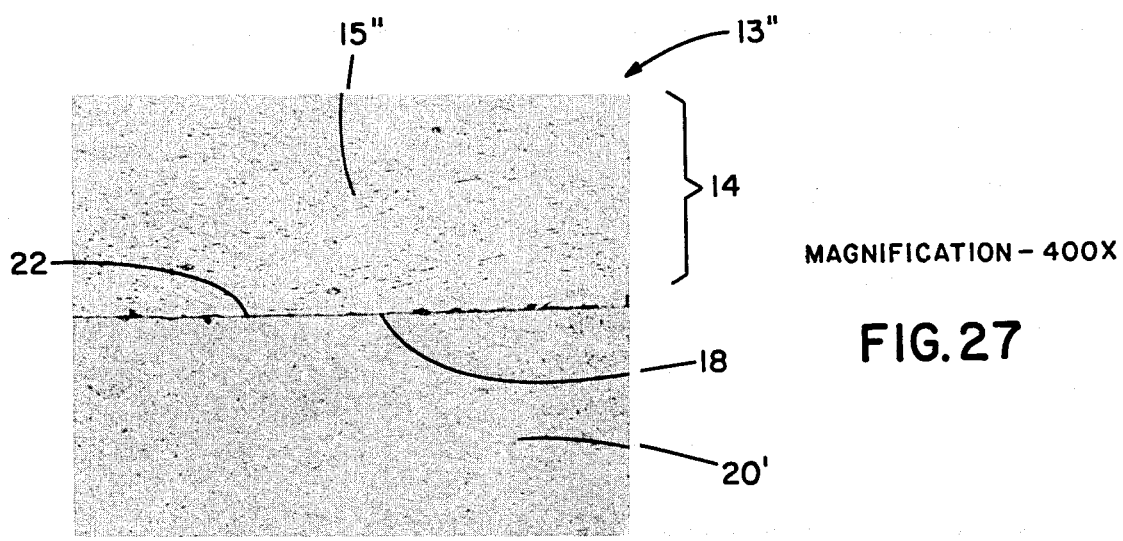

FIG. 11 is a photomicrograph (6X) of a porous body, identical to that illustrated in FIG. 1, resistance forge welded in accordance with the present invention, to a substrate identical to that illustrated in FIG. 1, shown in the etched condition;

FIG. 12 is a photomicrograph (400X) of a porous body, identical to that illustrated in FIG. 1, which has been resistance forge welded in accordance with the present invention, to a substrate of 0.50 inch thick Ti - 6Al-4V annealed bar, taken at the juncture of the faying surfaces and shown in the unetched condition;

FIG. 13 is a photomicrograph (400X) identical to that shown in FIG. 12 except in the etched condition;

FIG. 14 is a photomicrograph (6X) of a porous body and solid substrate identical to that shown in FIG. 11, but revealing a heat affected zone in the substrate;

FIG. 15 is a photomicrograph (400X) of the heat affected zone in the substrate shown in FIG. 14, in the etched condition to reveal the microstructure of that zone;

FIG. 16 is a photomicrograph (400X) of the porous body and substrate shown in FIG. 11, taken at the faying surfaces and in the etched condition, and included herein so that the microstructure of the substrate without a heat affect zone can be directly compared to that of the heat affected zone shown in FIG. 15;

FIG. 17 is a photomicrograph (6X) of a porous body identical to that illustrated in FIG. 1, which has been resistance welded to a substantially solid substrate of 0.090 inch thick Ti- 6Al - 4V alloy coupon in accordance with the present invention shown in the etched condition to reveal a heat affected zone in both the porous body and substrate which comprises a fusion weld;

FIG. 18 is a photomicrograph (400X), showing a porous body fabricated from sinusoidally kinked (commercially pure) titanium wire, sinter bonded to a substrate comprising forged Ti - 6Al - 4V alloy, taken at the faying surfaces in the etched condition and showing the depletion of alloy from the substrate at the diffusion zone, grain growth across the faying surfaces, and the sharp, notched condition presented at the sintered bond;

FIGS. 19, 20 and 21 are photomicrographs (20X) of porous bodies, identical to that illustrated in FIG. 1, which have been resistance forge welded in accordance with the present invention, to solid substrates, also identical to that illustrated in FIG. 1 and all shown in the unetched condition. The resistance forge welding was carried out with varying electrode forces so that the forging pressure varied from 14,000 psi to 7,000 psi to 3,500 psi, respectively, while other welding parameters remained constant;

FIGS. 22 and 23 are photomicrographs (6X and 750X, respectively) of a porous body identical to that illustrated in FIG. 5, which has been resistance forge welded in accordance with the present invention to a 0.75 by 0.75 inch coupon of 0.090 inch thick sheet, shown in the etched condition;

FIG. 24 is a photomicrograph (40X) of porous body, identical to that illustrated in FIG. 1, which was resistance forge welded to a substrate without using an electrically conductive material to impregnate the porous body, as required by the present invention. The porous body was, however, impregnated with a mixture of sodium chloride and calcium dichloride;

FIG. 25 is a photomicrograph (400X) of a porous body identical to that illustrated in FIG. 1, which has been resistance forge welded to a substrate coupon (0.75 by 0.75 by 0.35 inch) comprising a nickel-based alloy having the trade name Inconel. The photomicrograph is taken at the juncture of the faying surfaces, with the sample in the unetched condition, and shows no discernable diffusion or alloying zone;

FIG. 26 is a photomicrograph (400X) of the porous body and substrate shown in FIG. 25 but in the etched condition;

FIG. 27 is a photomicrograph (400X) of a porous body substantially identical to that shown in FIG. 1 (except being fabricated from sinusoidally kinked, 316 stainless steel wire), which has been resistance forge welded to a substrate of Inconel in accordance with the present invention. The photomicrograph is taken at the juncture of the faying surfaces and the specimen is shown in the etched condition; and FIGS. 28 to 32 show various configurations of impregnating patterns and electrodes which may be used to practice the method of the present invention.

DETAILED DESCRIPTION OF THE INVENTION

Referring now to the drawings, and in particular to FIG. 1, there is shown a metallic porous body, generally indicated by reference numeral 13, which comprises a plurality of components 15 arranged in a three dimensional matrix so as to form a plurality of interconnecting pores or voids 17 between the components 15. The porous body 13 is in the shape of a right cylinder, the top flat face of which defines a faying surface 18. In accordance with the present invention, porous body 13 can be welded to a substantially solid, metallic substrate 20 which also defines a faying surface 22. The joinder of porous body 13 and substrate 20 is accomplished by the formation of metallurgical bonds between faying surfaces 18 and 22, carried out by the resistance welding method of the present invention.

In the porous body 13 illustrated in FIG. 1, the components 15 are filaments, substantially in the shape of a sinusoid, as is more clearly seen in FIG. 2. The sinusoidal filament components 15 are formed from commercially pure, grade I, titanium wire, 11 mils in diameter. The wire is sinusoidally kinked by passing it between a pair of spaced-apart but meshed gears. The kinked wire is thereafter cut into a plurality of components, i.e. short lengths of about one inch.

The sinusoidally kinked filament components 15 are deposited into a cylindrical cavity 23 formed in a steel die 25, as shown in FIG. 3. A matching ram 27 is used to compact the sinusoidal components 15 against a plug 29 located in the bottom of the die 25, thus molding the cylindrical porous body 13 shown in FIG. 1. For the experiments reported herein, a number of porous bodies were so fabricated, each being rammed to a density of about 44 percent of the metal or alloy from which the components were fabricated.

Because a substantial number of the filament components 15 in the rammed porous body 13 are in physical contact, there is established electrical communication between those components 15. That is to say, an electrical voltage applied across the faying surface 18 of the cylinder and any other point on the surface of the cylinder, will result in the flow of electrical current between the points of voltage application.

Referring now again to FIG. 2, it can be seen that the sinusoidal deformation of the filament component 15 defines a period, designated by the letter P, which is equal to the distance between adjacent crests 19 or troughs 21, measured in a direction parallel to the longitudinal axis L of the wave form. The amplitude of the wave, designated by the letter A, is defined as onehalf the distance between crests 19 and troughs, measured in a direction normal to the longitudinal axis L of the wave form. When fabricating a porous body by molding sinusoidally kinked components, it is preferable that the ratio of the amplitude to the period (A/P) be maintained at 0.24 or greater. If such a ratio is maintained, the filament components interlock on molding and the porous body has considerable mechanical strength without further treatment. The above-mentioned ratio of amplitude to period also works to promote a more uniform porosity in the body.

It will be understood by those skilled in the art that porous body 13 can be further strengthened by subjecting the same to an appropriate sintering cycle. Sintering can cause the formation of metallurgical bonds between the filament components 15 at their points of contact. Sintering of the porous body 13 is not, however, necessary to practice the method of the present invention.

FIG. 5 shows another embodiment of a porous body 13' which comprises a plurality of metallic components 15', substantially spherical in shape and arranged in a three dimensional matrix (again in the shape of a right cylinder) so as to form a plurality of interconnecting pores or voids 17 between the components 15'. Again, a substantial number of the components 15' are in physical contact and, therefore, in electrical communication. Porous body 13' also defines a faying surface 18 which can be welded to a substantially solid substrate 20 in accordance with the method of the present invention.

Porous body 13' is fabricated using the apparatus illustrated in FIG. 6. A graphite block 31 is milled to form a pair of cylindrical cavities 33. The cavities 33 are filled to the desired level with a plurality of spherical components 15, (commercially pure, grade II, $-30 +45$ Tyler mesh titanium powder). A matching graphite ram 35 is inserted in each cavity 33 over the spherical components. A secondary graphite slab 37 and a one pound titanium block 38 are placed over the graphite rams 35. The entire assembly is then vacuum sintered at 1200° C. for two hours, thereby forming metallurgical bonds between the individual spherical components 15' at their points of contact. The graphite block 31 is then broken away and right cylindrical porous bodies 13' removed.

The electrical resistance of unimpregnated porous bodies 13 and 13' were measured with a milli-ohm meter and found to be between about 3 and 5 milli-ohms.

Referring now to FIGS. 4 and 7, there is shown porous bodies 13 and 13' respectively, which have been impregnated with an electrically conductive material 39 (which is magnesium in this illustrated embodiment) to a predetermined distance D from their faying surfaces 18, thus defining unimpregnated zones 14 and impregnated zones 16. That is to say that the interconnecting voids, or pores, 17, between the components 15 and 15', located a distance D, or greater, from the faying surface 18 have been filled with electrically conductive material, magnesium 39.

Figure 8:
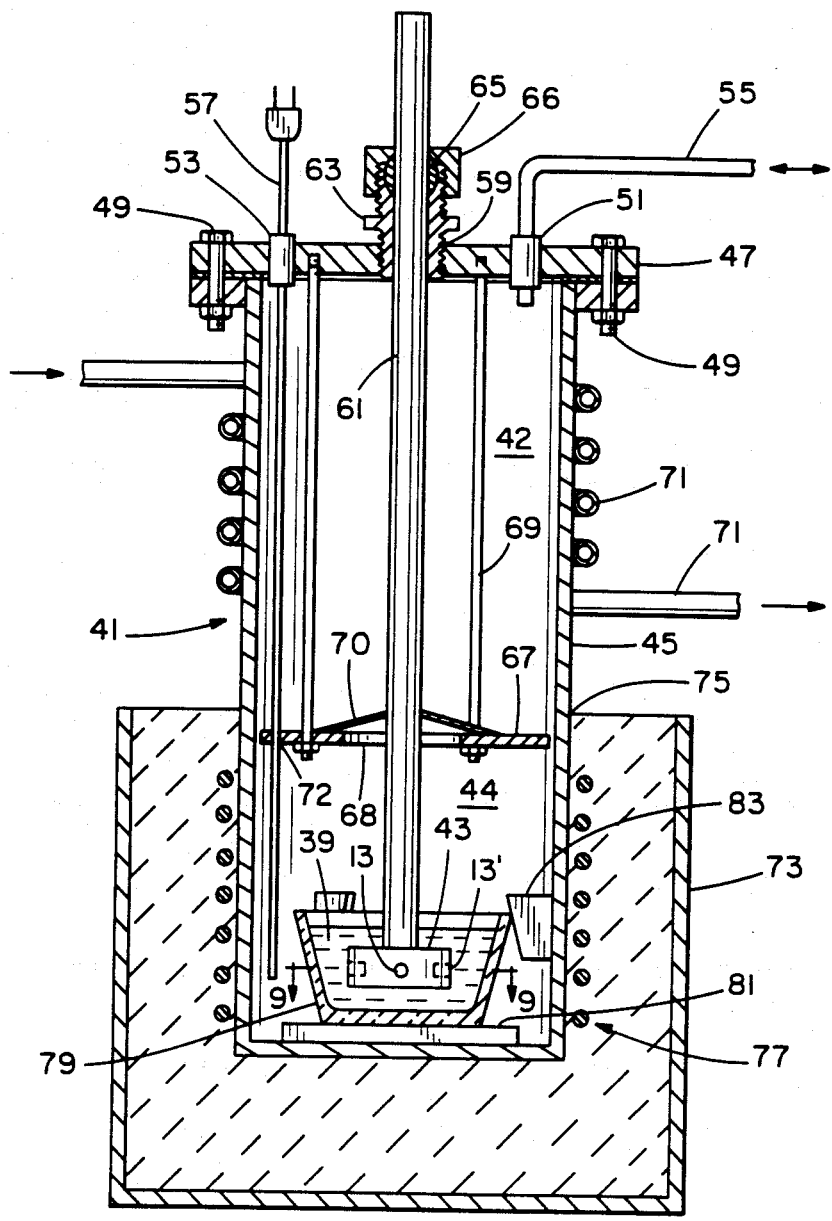
FIG. 8 is a front elevation, shown in partial cross section, of a retort, well furnace, and associated equipment used to impregnate the porous bodies shown in FIGS. 1, 4, 5 and 7.

The step of impregnating porous bodies 13 and 13' is readily carried out by an immersion process (followed by etching), using the retort 41 and fixture 43 illustrated in FIGS. 8 and 9. The retort 41 comprises a steel housing 45 fitted with a removable, gas-tight lid 47 which is held in place by a plurality of fasteners 49. The lid 47 has apertures 51 and 53 which received gas conduit 55 and a thermocouple 57, respectively. A third aperture 59 provides access to a molybdenum plunger rod 61. Each aperture is made gas tight by virtue of a compression fitting 63 which includes a deformable ferrule 65 and compression nut 66. For purposes of clarity, only the compression fitting 63 about plunger rod 61 is shown in the drawing.

Retort 41 is divided into a relatively cool zone 42 and a relatively hot zone 44 by a heat shield 67 suspended from the lid 47 by threaded rods 69. Heat shield 67 has an opening 68 formed in its center which permits passage of plunger rod 61 therethrough. A piece of tantalum foil 70, loosely wrapped about the plunger rod 61 helps to seal opening 68. The temperature in the retort hot zone 44 is maintained by an electrical resistance furnace 73, which receives the retort 41 in a well 75 having heating elements 77. The temperature in hot zone 44 is measured by thermocouple 57 which is passed through a second small opening 72 in heat shield 67. The temperature in the retort cool zone 42 is maintained relatively cool by virtue of heat shield 67 and a water jacket 71 through which cooling water is circulated.

A titanium crucible 79 is placed at the bottom of retort 41, in the hot zone 44, on a graphite block 81. Graphite wedges 83 secure the position of crucible 79 in the center of the retort. Crucible 79 is filled with the electrically conductive impregnating material 39, magnesium.

Referring now to FIG. 9 it can be seen that porous bodies 13 and 13' are press-fitted in radial receptacles 9, formed in graphite fixture 43. Fixture 43, with porous bodies 13 and 13' mounted therein, is secured to the bottom end of plunger rod 61 by means such as wire. Plunger rod 61 is drawn up so that fixture 43 is held in cool zone 42 while heat is applied to hot zone 44 to cause melting of the magnesium 39. Air is pumped from retort 41 and replaced by argon gas through conduit 55 to prevent oxidation of the magnesium.

Once the magnesium 39 has been melted and raised to the proper temperature, plunger rod 61 is lowered so that fixture 43 containing porous bodies 13 and 13' are fully immersed. Compression nut 65 is tightened to prevent air leaks about plunger rod 61 and a vacuum of about $10^{-3}$ mm of mercury is drawn in the retort 41. This vacuum is held while the fixture 43 and porous bodies 13 and 13' come to thermal equilibrium with the molten magnesium 39, about three to five minutes. Argon is then reintroduced to return the retort 41 to atmospheric pressure. Compression nut 65 is loosened and plunger rod 61 is raised so that fixture 43 and porous bodies 13 and 13', now fully impregnated, are raised into cool zone 42. The temperature of cool zone 42 is maintained low enough so that the magnesium 39 in porous bodies 13 and 13, freezes solid and does not ignite upon removal to the atmosphere.

The interconnecting pores 17 in porous bodies 13 and 13' are now fully impregnated with solid magnesium 39. Magnesium is then removed to a predetermined distance, D, away from the faying surfaces 18 of porous bodies 13 and 13'. In the illustrated embodiment of the method of the invention, this was accomplished by swabbing the faying surface 18 with dilute HCl and rinsing the surface 18 with water to stop the etching action. While magnesium is vigorously etched by HCl, titanium is very resistant to this acid. An acid-resistant mask applied to the exterior surfaces of the porous bodies, to the desired distance, D, below the faying surface 18, greatly facilitates controlling the etching depth of the HCl. By this process, porous bodies 13 and 13', as shown in FIGS. 4 and 7, were impregnated with an electrically conductive material, magnesium 39, to a predetermined distance from their faying surfaces 18, thus forming unimpregnated zones 14 and impregnated zones 16.

In the preferred embodiment of the invention, the components 15 and 15' in the porous bodies 13 and 13' are fabricated from a metal or alloy having a relatively high melting point or solidus temperature, such as titanium. Conversely, the electrically conductive impregnating material 39 is preferably a metal or alloy having a relatively low melting point or liquidus temperature such as lead, lithium, magnesium, aluminum, zinc or calcium and their alloys. This differential in melting or freezing temperatures (or, in the case of alloys, liquidus and solidus temperatures) facilitates impregnation of the porous bodies by immersion in a molten pool of the electrically conductive material 39.

The aforemention metals and their alloys are specifically mentioned because of their ready availability, relatively low cost and relative stability in the atmosphere. Other suitable metals, which may be undesirable only because of their chemical instability in ambient atmosphere, include elemental sodium and potassium. Other, more exotic metals and alloys may possess desirable features such as a relatively low melting point and chemical stability but be prohibitively expensive. As will become clear to those skilled in the art, the most important features of the electrically conductive impregnating material are the ability to carry electrical current, without melting, during the welding method of the present invention, and, in the preferred embodiment, the ability to give mechanical support to the impregnated zone so that the unimpregnated zone can be densified and forge welded to the substrate, without sacrificing the porosity of the impregnated zone.

Also in the preferred embodiment of the invention, the electrically conductive impregnating material 39 is chosen so as to have little, if any effect on the chemistry or microstructure of the metal or alloy which comprises the porous body. When porous bodies are fabricated from titanium or its alloys such as 13 and 13′, and especially when impregnation is carried out by immersion, calcium, magnesium or alloys thereof are the preferred choices for the electrically conductive impregnating material 39. These materials are preferred for three reasons: the melting point of titanium is substantially higher than that of calcium, magnesium or their alloys; the solubility of titanium is negligible in calcium, magnesium or their alloys at temperatures just above but near their melting points or liquidus temperatures; and the solid solubility of these metals in titanium is negligible at the same temperatures. Any minor dissolution of titanium from the porous body which could occur by immersion in a fresh pool of the preferred impregnating material, can be minimized by first saturating the molten impregnating material with another source of titanium. This is readily accomplished by maintaining the molten pool of impregnating material in a titanium crucible and allowing the pool to reach chemical equilibrium before immersing the titanium porous body therein.

It has been found that the components in a molded porous body 13, can be metallurgically bonded together by maintaining the molded body 13 immersed in the molten electrically conductive impregnating material 39 at temperatures and for times which correspond to vacuum sintering. Thus, the steps of impregnation and bonding of components 15 can be combined. Such a combination works quite well for titanium porous bodies, sintered in and impregnated with magnesium.

Finally, it is preferable that the electrically conductive impregnating material 39 be readily removable from the porous body, after the welding method of the invention has been carried out. For instance, if a porous body fabricated from titanium is impregnated with magnesium or a magnesium-based alloy, and resistance forge welded to a substrate of titanium, immersion of the porous body in a sufficient quantity of dilute hydrochloric acid results in removal of substantially all the magnesium. The magnesium is etched from the porous body without substantially affecting the titanium. The use of calcium as the impregnating material has the added benefit of being removable in water.

Figure 10:
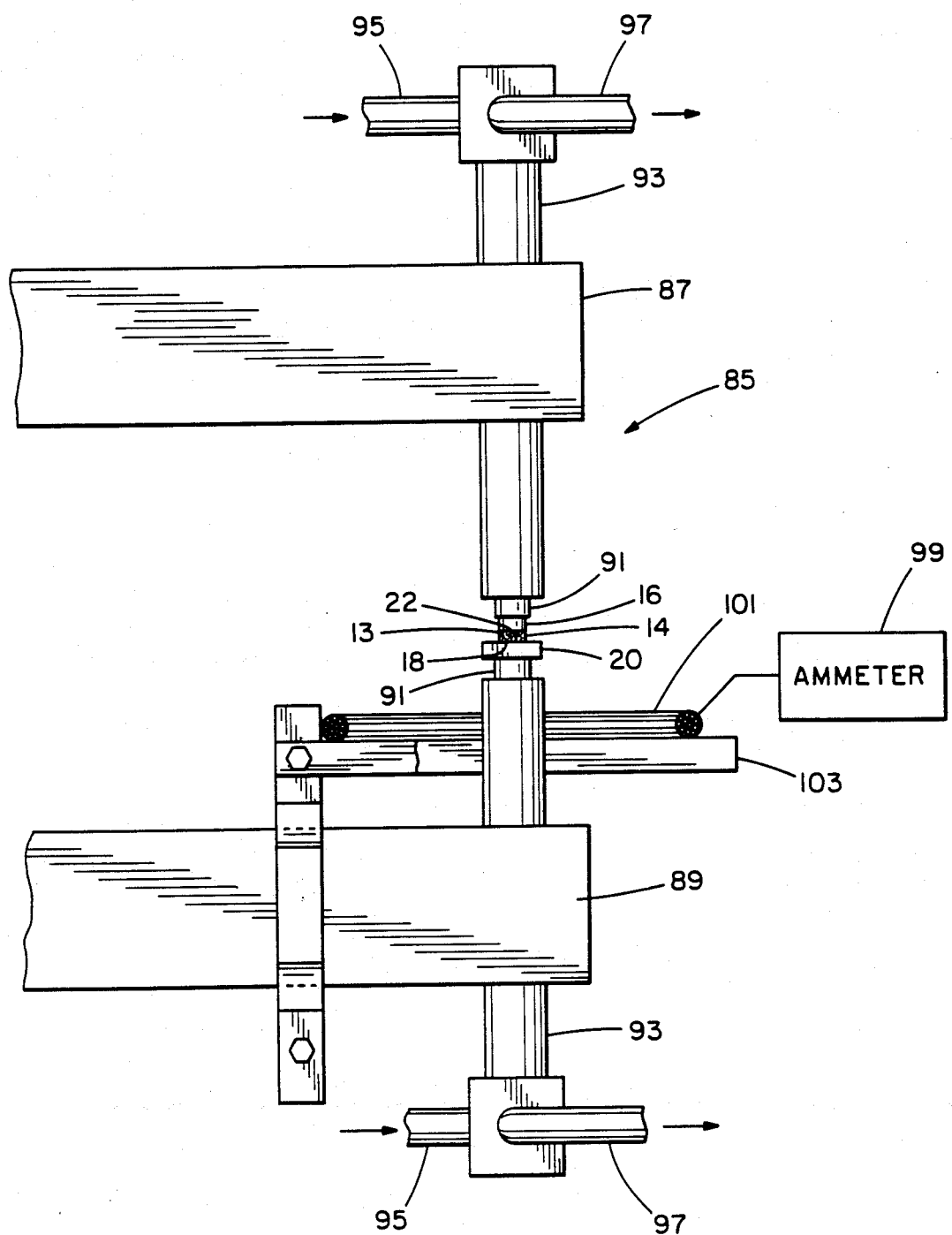
FIG. 10, is a partial, side elevation of an electrical resistance welding apparatus, taken about the vicinity of the electrodes and which was used to weld the porous bodies shown in FIGS. 1, 4, 5, and 7 to substantially solid substrates, such as that illustrated in FIG. 1.

FIG. 10 illustrates the welding apparatus 85 which was used to pass an electrical current through porous bodies 13 and 13′ and substrates 20 associated with each, across faying surfaces 18 and 22, forming metallurgical bonds therebetween. For each of the samples shown in the photomicrographs in FIGS. 11 through 27 (excluding FIG. 18), welding apparatus 85 was employed. The apparatus 85 is commercially available and is a 30 KVA electrical resistance spot welder, manufactured by Lors Machinery, Inc.

The apparatus 85 includes an electrical transformer (not shown) which creates a voltage across top 87 and bottom 89 horns. The longitudinal axes of the horns are generally horizontal and aligned in a vertical plane. Associated with each horn, and in electrical communication therewith, is a cylindrical electrode 91, mounted with its axis substantially normal to and in the same plane as the axes of the horns 87 and 89. A water jacket 93 having inlet 95 and outlet 97 conduit is used to keep the electrodes cool during the welding process. The voltage applied across horns 87 and 89, and therefore the voltage across electrodes 91 and, ultimately porous body 13 and substrate 20, is regulated by a tap (not shown) associated with the welding apparatus' 85 transformer. Very precise regulation of the voltage, and the duration of the voltage application, was achieved by the use of a controlling unit, sold under the trade name Technitron MCS 2009 Microcontroller.

Top horn 87 is movable in the direction of the longitudinal axes of cylindrical electrodes 91, so that pressure can be exerted on a porous body 13 and substrate 20 which has been placed between electrodes 91. The movement of top horn 87, and the force created thereby, is pneumatically activated so that the pressure generated between the porous body 13 and substrate 20 can be controlled by a pressure regulating valve (not shown) associated with top horn 87.

The application of a voltage across electrodes 91 in resistance spot welder 85 results in the flow of electrical current through the work piece (in this instance a porous body, impregnated in accordance with the invention, and substrate). The magnitude of the current which flows through the work piece is directly proportional to the electrical resistance of the work piece and the magnitude of the voltage which is applied. The energy dissipated and converted to heat during a welding process of a given duration, is directly proportional to the current density in the work piece. Thus, if the welding cycle is sufficiently short so that heat losses during the cycle can be ignored, the current density in the work piece can be used as a parameter to establish the necessary conditions for producing an acceptable weld.

For the welding experiments conducted in accordance with the present invention and reported herein, an ammeter 99, capable of measuring a transient current, was used to determine the current density in the porous body and substrate during the welding cycle. The ammeter 99 included an induction coil 101 which was centered about bottom electrode 91 with the aid of a wooden bracket 103. Wood was chosen as the material for the bracket 103 to prevent the induction of stray currents which could work to produce false readings from the ammeter. The ammeter 99 and associated coil 101 (model no. TSU-250) were manufactured by Digimetrics, Inc. (4947 Commercial Drive, Yorkville, N.Y. 13495).

In accordance with the present invention, porous bodies such as 13 and 13', were first impregnated with an electrically conductive material to a predetermined distance from their faying surfaces 18, as previously described. For the porous bodies appearing in the photomicrographs in FIG. 11 through FIG. 27, unless otherwise indicated, magnesium was used as the electrically conductive impregnating material. As illustrated in FIG. 10, faying surface 18 of the porous body 13 was then brought into contact with faying surface 22 of substrate 20. (It will be understood by those skilled in the art that description of the welding of porous body 13 is exemplary and that the welding process of the invention can be used in conjunction with any porous body as defined herein, such as 13'.) The porous body 13 and substrate 20 were then located between top and bottom electrodes 91 as shown in FIG. 10 and gently held in place by low pressure-activated movement of horn 87. In this configuration, impregnated zone 16 is in direct contact with upper electrode 91 and unimpregnated zone 14 is disposed between faying surface 22 and impregnated zone 16. After location of the porous body and substrate, a much higher, predetermined welding pressure is applied to the assembly of the porous body 13 and substrate 20 through horn 87. Shortly after establishing the proper welding pressure, a predetermined voltage is applied across horns 87 and 89, causing current to flow through the porous body 13 and substrate 20, across faying surfaces 18 and 22, for a predetermined duration. The electrically conductive material 39 in the impregnated zone 16 of the porous body 13 lowers the electrical resistance in that zone so that the unimpregnated zone 14 is preferentially heated to a much higher temperature. It is preferred that the welding pressure be maintained for a period of time sufficient to permit the porous body and substrate to cool well below the hot working temperature, after application of the welding current. This cooling is aided by the water jacket 93 which cools electrodes 91. It should be noted that the direction of the force applied to porous body 13 or and substrate 20 is substantially normal to faying surfaces 18 and 20. An application of force sufficient to cause 14,000 psi pressure between the faying surfaces and (60 Hz ac) voltage of sufficient magnitude to cause a peak (as opposed to RMS) current density equal to or greater than 150,000 amperes per square inch of faying surface, for a duration of at least five cycles (1/12 of a second), was found to result in welding, or the formation of a metallurgical bond between the faying surfaces.

The method of the present invention is preferably used to form a "forge weld" between a porous body and substrate. As used herein, the term "forge weld" means the joinder of (or act of joining) at least two metal members (such as a metal body and a metal substrate), each of which defines a faying surface and a zone adjacent thereto, which joinder or act of joining is carried out by: heating the aforesaid adjacent zone in one or both of the members, preferably to the hot-working temperature of the metal or alloy of the heated zone or zones; bringing the faying surfaces of the members into contact; and forcibly pressing the members together with a force, which force is or has a vector component that is, substantially normal to the faying surfaces and which force or component is of sufficient magnitude to cause plastic deformation in the heated zone of at least one of the members, all of which results in metallurgical bonding between the members at the juncture of the faying surfaces.

The above definition of "forge weld" includes the term "hot-working temperature". As used herein, this term has the generally accepted definition used by those skilled in the art of metallurgy. The "hot-working temperature" of a metal or alloy is generally defined as a temperature range having an upper limit below the melting point of the metal or solidus of the alloy and a lower temperature limit defined as the lowest temperature at which plastic deformation of the metal or alloy results in no appreciable residual strain hardening. Thus, the lower limit of "hot working temperature" is generally linked to that temperature at which recrystallization of the metal or alloy occurs at a relatively rapid rate, i.e. generally in a time that is of the same order as the rate of plastic deformation.

A welding current density (calculated from the measured, peak current, 60 Hz a/c, and the area of contact between the faying surfaces) greater than or equal to about 150,000 but less than or equal to about 170,000 amperes per square inch of faying surface for, a duration of 5 cycles, with a welding pressure of 14,000 psi (also calculated from the area of contact between the faying surfaces), was found to produce satisfactory forge welds, without a heat affected zone in the substrate, between titanium porous bodies and titanium substrates of the types illustrated in FIGS. 1 and 5. With all other parameters constant, a current density less than about 150,000 amperes per square inch resulted in a failure to form a metallurgical bond between the faying surfaces. Similarly, a current density greater than about 170,000 amperes per square inch, for a duration of 5 cycles was also found to produce a satisfactory forge weld but resulted in the generation of a eat affected zone in the substrate. The energy input from a current density greater than about 200,000 amperes per square inch, for a duration of at least 7 cycles, was required to melt the substrate and a portion of the porous body, that is to form a fusion weld. This relationship between current density, the type of weld produced and the presence or absence of a heat affected zone was found to be substantially independent of the thickness of the titanium substrate (for substrates having thicknesses greater than or equal to 0.090 inch).

It is believed that the relationship between welding parameters (such as current density, the duration of current application and forging pressure) and the character and quality of the weld (whether no weld, a forge weld or fusion weld is formed and whether or not the welding produces a heat affected zone) will vary, depending upon the density and overall geometry of the porous body, the type of metal or alloy used to fabricate the porous body and substrate and the type of electrically conductive impregnating material which is used.

To practice the preferred forge welding method of the invention, the duration of the application of welding current should be sufficiently short to take advantage of the temperature differential created between the unimpregnated zone and impregnated zone in the porous body. The electrically conductive impregnating material acts to lower the electrical resistance of the impregnated zone so that the initial heating from the application of welding current results in a lower temperature than is obtained in the unimpregnated zone. The electrically conductive impregnating material can also act a heat sink to draw heat away from the components in the impregnated zone. In addition, the electrically conductive material bears a substantial portion of the welding pressure in the impregnated zone, thus preventing its collapse during the forge welding operation. If the duration of the application of welding current is too long, the heat generated in the unimpregnated zone can be absorbed by the electrically conductive impregnating material. If the electrically conductive impregnating material reaches it hot-working temperature or its melting point or solidus, it loses its load-bearing characteristics, which causes collapse of the impregnated zone from the welding pressure. Thus, the magnitude and duration of the welding current must be great enough and long enough to cause the unimpregnated zone to reach its hot-working temperature; but low enough and short enough to prevent heating of the electrically conductive impregnating material to its hot-working temperature or melting point or solidus.

It is clear then, that the duration of the application of welding current which results in a forge weld, depends upon a number of factors, including the magnitude of the current density and the thermal mass of the impregnated porous body. It is contemplated, however, that for most applications, the size of the forge weld will be on the order of those shown in the experiment reported herein. Thus, the duration of the application of welding current is preferably maintained as short as possible and preferably not for a time exceeding one second.

The strength of the bond between a porous body and substrate that is required, clearly depends on the application. In some instances, such as in the case of fluid filters, where heavy loading is not anticipated, a few spot welds produced in accordance with the invention may suffice. In other instances, such as in the case of orthopedic prosthetic devices, an extremely good bond is required between the porous body and load-bearing substrate. The forge welds described herein and illustrated in the photomicrographs were tested for strength by tensile loading of the porous body, carried out to failure. This test resulted in tensile failure of the porous body above the densified unimpregnated zone. This clearly shows that the metallurgical bond between the faying surfaces was of higher strength than the matrix of components in the unimpregnated zone of the porous body.

Application also determines whether a heat affected zone in the substrate is tolerable. It is important to note that the method of the present invention can be used to form a forge weld, between a porous body and substrate, without generating a heat affected zone in the substrate and where the forge weld has a greater tensile strength than the tensile strength of the porous body. Such a result may be necessary when the substrate is load-bearing and subjected to the type of cyclic loading that can generate fatigue failures. The elimination of a heat affected zone in the substrate of orthopedic prosthetic devices is clearly desirable.

It will, however, be understood by those skilled in the art, that a heat affected zone which is readily observed in a macroscopic examination, may, in fact, comprise such minor changes in the microstructure of the metal or alloy as to be insignificant in its effect upon the mechanical properties of the metal or alloy. It is the degree of change in the microstructure of the heat affected zone which dictates mechanical performance. For instance, the greatest change in microstructure which can result from a welding process, is observable in a fusion weld. Such a weld is readily obtainable by the method of the present invention, but may, in many instances be considered undesirable. A fusion weld often results in a substantial loss of strength and fatigue resistance, due to the grain structure of the resolidified metal or alloy, and alloying of the porous body and substrate when dissimilar metals or alloys are joined.

Referring now to FIG. 11, there is illustrated a good forge weld, which was obtained in accordance with the present invention, between a porous body 13 and substrate 20. After forge welding, the porous body and substrate were immersed in a solution of dilute hydrochloric acid to remove the electrically conductive impregnating material, magnesium. The body and substrate were then sectioned with a diamond saw, the cut being made in a direction normal to the faying surfaces 18 and 22. One half of the specimen was then mounted in epoxy with the cut face exposed. The specimen was then ground, polished and etched (one part 50% reagent grade hydrofluoric acid, one part 70% reagent grade nitric acid and three parts glycerin) in accordance with standard metallographic techniques.

FIG. 11 clearly shows that the unimpregnated zone 14 has been densified to the point of near zero porosity and that the impregnated zone 16 has retained full porosity. In fact, the components 15 in the unimpregnated zone have been forge welded together to form a substantially solid mass, which has in turn been forge welded to faying surface 22. Thus, the area of bonding between the porous body 13 and the substrate 20 comprises substantially the entire area of faying surface 18. The geometry of the metallurgical bonds between the porous body 13 and substrate 20 do not present a notched condition, as occurs when sinter bonding is employed (see FIG. 18 for comparison). It should also be noted that this forge weld was produced without generating observable changes in the microstructure of the substrate, i.e. creating a heat affected zone.

FIGS. 12 and 13 show a high magnification (400X) of the juncture between faying surfaces 18 and 22, of another forge weld created in accordance with the invention and between a titanium porous body 13, like that illustrated in FIG. 1, and a substrate 20 comprising a piece of titanium bar stock. In FIG. 12, the specimen is in an unetched condition, which reveals that the resulting forge weld is so dense and complete that the individual wire components and the actual juncture between the porous body and substrate is barely discernable. FIG. 13 is a photomicrograph of the same location on the same specimen, but with the specimen in the etched condition. The etchant attacked the high energy areas of the weld zone, i.e. the juncture between individual wire components and the juncture between wire components and the substrate. FIG. 13 shows the result of the plastic flow of components 15 and the virtually complete densification of the unimpregnated zone 14. It should be noted that the geometries of the bonds between the individual components 15 and between the components 15 and faying surface 22 of the substrate 20 are substantially contiguous over the entire surface of the components 15 and faying surface 22. Thus, the bond area has been maximized and the bond configuration does not present a notched condition.

Close inspection of FIGS. 12 and 13 also reveals an important result from using the forge welding method of the invention. There is no discernable zone of diffusion between the porous body 13 and the substrate 20. Thus, it is reasonable to assume that the mechanical properties of the porous body 13 and substrate 20 have not been changed as a result of gaining or losing alloying elements. The importance of this result is best appreciated when a porous body and substrate, which comprise dissimilar base metals or alloys, are forge welded in accordance with the invention. Thus, it is believed that the method of the present invention can be used to overcome the tendency of some dissimilar materials to form brittle intermetallic compounds upon joinder, as occurs when conventional means, such as fusion welding, brazing or sintering, are employed.

FIG. 14 shows a low magnification (6X) photomicrograph of a porous body 13, which has been resistance forge welded in accordance with the present invention, to a substrate 20. In this instance, the welding resulted in a heat affected zone 115 in the substrate 20. FIG. 15 shows a high magnification (400X) photomicrograph of the heat affected zone 115, in the etched condition, so as to reveal the microstructure of the heat affected substrate. This microstructure should be compared to FIG. 16, which shows the microstructure of an identical substrate without a heat affected zone, i.e. the substrate 20 of the sample shown in FIG. 11. It will be noted by those skilled in the art that while the heat affected zone 115 in FIG. 14 is clearly visible by macroscopic examination, the change in the microstructure of the substrate alloy is minimal. Thus, it is not expected that the mechanical properties of the heat affected zone 115 in the substrate 20 of the sample shown in FIGS. 14 and 15, vary by any substantial degree from those of the substrate in the sample shown in FIGS. 11 and 16.

Referring now to FIG. 17, there is shown a low magnification (6X) photomicrograph of a porous body 13 resistance welded to a substrate 20 in accordance with the present invention. FIG. 17 reveals that the welding process resulted in the formation of a fusion zone 117 which appears to encompass both the substrate 20 and a portion of the unimpregnated zone 14 of the porous body 13. The fusion zone 117 shows characteristic columnar grains which appear as a result of solidification from a molten state. A substantial portion of the unimpregnated zone 14 also appears to have been forge welded. It is likely that the electrically conductive impregnating material (magnesium) melted to some degree during the welding process, so that the components 15 in a portion of the impregnated zone 16 also forge welded together. It is clear, however, that some degree of porosity was retained in the impregnated zone 16.

As previously mentioned, it is believed that a weld structure which consists entirely of a forge welded structure is preferable. FIG. 17 is included, though, to show that it is possible to obtain a fusion weld between a porous body and a substrate by the method of the present invention.

FIG. 18 is a high magnification (400X) photomicrograph of a porous body, fabricated from sinusoidally kinked, commercially pure, titanium wire components 15, similar to that illustrated in FIG. 1, but which has been affixed to a substantially solid substrate 20 of forged Ti - 6AL - 4V alloy, via vacuum sintering. The specimen is shown in the etched condition to reveal the substantial changes in the microstructure which have been brought about by the sintering process. The microstructure of the specimens shown in FIGS. 11, 12, 13, and 16 and the geometry of the bonds disclosed therein (obtained by the preferred method of the invention), should be compared to that shown in FIG. 18.

FIG. 18 shows a clearly discernable diffusion zone, indicated by a bracket and reference numeral 121, which bridges the wire component 15 and substrate 20. The difference in the appearance of this diffusion zone (as compared to the balance of the substrate), suggests that the alloying elements (Al and V) have been depleted from the substrate 20 to an appreciable distance below the faying surface 22, directly in the vicinity of the bond. In addition, substantial grain growth has resulted in large, single grains bridging the component wire 15 and substrate 20. It is reasonable to assume that this grain growth and the depletion of alloy from the substrate in the bond area, both work to lower the strength and fatigue resistance of the substrate 20. The aforesaid reduction in strength and fatigue resistance is further exacerbated by the geometry of the bond between the wire components 15 and substrate 20. Without densification of the porous body in the zone directly adjacent the faying surface of the body (as is obtained by the preferred method of the present invention), the area of contact between the components 15 and substrate 20 is limited. This limited area of contact results in a configuration wherein the wire component 15, in conjunction with the substrate 20, presents a notch 123. Furthermore, the notch 123 has a root 125 which is directed toward the diffusion zone 121, wherein the mechanical properties of the substrate 20 have been most severely compromised. The application of repeated shear or tensile stresses between the porous body 13 and substrate 20, invites the initiation and growth of a fatigue crack at notch root 125.

In the case of prosthetic orthopedic devices, the bonds between the components 15 and substrate 20 transfer loads from the bone of the patient to the load-bearing substrate of the device. Cyclic loading of the porous body is frequently encountered, for instance, in prosthetic hip devices, as the patient walks or runs. It is believed that the method of the present invention can be utilized in the fabrication of such prosthetic devices to substantially increase their fatigue life.

Referring now to FIGS. 19 through 21, inclusive, there is shown a series of relatively low magnification (20X) photomicrographs of porous bodies 13 which have been resistance forge welded to substrates 20, in accordance with the present invention. The only parameter which was varied during the welding process was the pressure exerted by the electrodes. For each specimen, the welding current density was about 153,000 amperes per square inch of faying surface contact and the welding time was 5 cycles. The pressure exerted on the specimens by the pneumatically activated top horn 87 was 14,000 psi, 7,000 psi and 3,500 psi for FIGS. 19, 20 and 21 respectively.

The photomicrographs clearly show that regardless of the welding pressure, the porosity was retained in the impregnated zone 16 and that the unimpregnated zone 14 was densified. It is important to note, however, that the degree of densification of the unimpregnated zone, increased with increasing welding pressure. It is also important to note that the total weld area (the area of metallurgical bonding), at the juncture of faying surfaces 22 and 18, increased with increasing weld pressure. Likewise, the number of voids, or unwelded zones at the juncture of the faying surfaces, decreased with increasing weld pressure. Finally, it should be noted that the configuration of the components 15 at the faying surface 18, in conjunction with faying surface 22 of the substrate 20, become less "notch-like" as welding pressure is increased.

Thus, it is clear that increasing weld pressure, in the preferred forge welding process of the present invention, can benefit the bonding between the porous body 13 and substrate 20. Increasing weld pressure does, however, have a point of diminishing returns. Too high a weld pressure can overcome the mechanical support offered to the impregnated zone by the electrically conductive material, and result in a substantial loss of porosity in the impregnated zone. An acceptable weld pressure is then governed by a number of variables, including the mechanical properties of the electrically conductive impregnating material, the temperature to which the impregnating material is heated by the application of welding current and the degree of lost porosity which is considered acceptable.

The movement of pneumatically activated horn 87, and electrode 91 associated therewith, is also clearly limited by the porous body 13 or 13' itself. In the preferred embodiment of the invention, impregnated zone 16 undergoes no densification. Furthermore, the degree of densification of the unimpregnated zone is a matter of choice, the degree of which can be controlled by appropriate weld pressure. Thus, movement of the electrode 91 is limited by the height of the impregnated zone 16 plus the height of the densified unimpregnated zone 14. The lower and upper limits of electrode movement are therefore, determined and limited by the difference in heights of the unimpregnated zone in the fully densified and uncompressed conditions.

Referring now to FIG. 22, there is shown a low magnification (6X) photomicrograph of a porous body 13, (identical to that illustrated in FIGS. 5 and 7 and described herein) fabricated from titanium bead components 15' (in accordance with the procedure previously described). Porous body 13, was impregnated with magnesium (to a predetermined distance from the faying surface 18) and resistance forge welded to a substrate 20 which comprises a 0.75 by 0.75 inch coupon cut from a sheet of 0.090 inch thick Ti - 6Al - 4V alloy. The welding process of the invention produced a heat affected zone 115, similar in configuration and severity to that shown in FIG. 14. As with the porous bodies 13 fabricated from titanium wire components 15, the unimpregnated zone 14 was densified to near zero porosity.

FIG. 23 shows a high magnification (750X) photomicrograph of the specimen shown in FIG. 22, taken at the juncture of the faying surfaces 18 and 22. This photomicrograph reveals the plastic deformation of components 15' (originally spherical) in the unimpregnated zone 14. The forge wedded shape of the components 15' closely resembles a cube. Prior to forge welding, the area contact between the spherical components 15' and substrate 20 was substantially point contact. After forge welding in accordance with the present invention, a planar area of metallurgical bonding has been established.

FIG. 24 is a relatively low magnification (40X) photomicrograph of a porous body 13 (identical to the porous body illustrated in FIG. 1) resistance forge welded to a substrate 20, without benefit of being impregnated with an electrically conductive material. The porous body 13 was impregnated with a mixture of sodium chloride and calcium dichloride to a predetermined distance from the faying surface 18. This mixture is substantially nonconducting and application of the welding current resulted in substantially uniform heating of the porous body. Thus, in order to heat the unimpregnated zone 14 to a temperature sufficient to cause forge welding, it was necessary that the impregnated zone 16 also reach approximately the same temperature. This resulted in melting of the salt mixture impregnating material and collapse and densification of the entire porous body 13. Thus, sufficient electrical conductivity of the impregnating material is critical to practice of the invention.

FIGS. 25, 26 and 27 are high magnification (400X) photomicrographs of porous bodies which have been resistance forge welded in accordance with the present invention to substrates comprised of dissimilar base alloys. The photomicrographs are all taken at the juncture of the faying surfaces 18 and 22.

FIG. 25 shows a porous body 13 (fabricated from commercially pure titanium wire components and identical to that illustrated in FIG. 1) which has been resistance forge welded to a 0.344 inch thick substrate 20' which is comprised of a nickel-based alloy, sold under the name Inconel. FIG. 26 shows the same forge welded specimen, but in the etched condition. A welding current density of 223,000 amperes per square inch of faying surface, over a duration of 5 cycles (1/12 second) and 14,000 psi welding pressure were the weld parameters employed. As previously mentioned, the forge welding method of the present invention prevents the formation of a discernable diffusion or alloying zone, when dissimilar base alloys or metals are joined. Neither FIG. 25 nor FIG. 26 reveal such a zone.

FIG. 27 is a high magnification (400X) photomicrograph of a porous body 13" (substantially identical to that illustrated in FIG. 1 except fabricated from 9 mil, sinusoidally kinked wire components 15" of 316 stainless steel) which has been resistance forge welded in accordance with the present invention to a substrate 20, of 0.344 inch thick Inconel. The welding parameters which were employed included a welding current density of 208,000 amperes per square inch of faying surface, for a duration of 5 cycles and a welding pressure of 14,000 psi. The specimen is shown in the etched condition and also shows no discernable diffusion or alloying zone.

Although no photomicrograph is included herewith, the welding method of the present invention was used to bond a porous body, fabricated from commercially pure titanium wire filaments, to a substrate comprising the previously mentioned Co - Cr - Mo alloy. This was accomplished by placing a 4 mil thick sheet of aluminum foil between the faying surfaces of the substrate and the unimpregnated zone of the porous body. A welding current of about 189,000 amperes per square inch of faying surface contact, for a duration of 5 cycles and a welding pressure of 14,000 psi resulted in a good forge welded bond. The aluminum was readily removed by etching with a sodium hydroxide solution.

Attempts to directly join these materials by resistance forge welding, without an intermediate layer of aluminum foil, proved unsuccessful (i.e. a reasonably high strength bond between the faying surfaces was not obtained). Attempts to form a less desirable fusion weld (using higher current densities) were successful. A wide range of welding parameters was not, however, attempted. Accordingly, there may be a combination of welding parameters that will permit the direct forge welding of these dissimilar alloys. In addition, the application of a suitable fluxing compound, such as an acid, may prove helpful to forming a forge welded bond.

FIGS. 28 through 32, inclusive, show various configurations of electrodes 91 and impregnating patterns for practicing the method of the invention. The electrode configurations and polarities disclosed in these figures are commonly used to practice electrical resistance welding between substantially solid members.

In FIG. 28, a porous body 13''' has been impregnated to include two impregnated zones 16, each a predetermined distance D from faying surface 18, leaving an unimpregnated zone 14 disposed between zone 16 and faying surface 18. Electrodes 91 are placed and have polarity so as to cause the welding current to flow across faying surfaces 18 and 22 to form metallurgical bonds therebetween.

FIG. 29 shows another impregnating pattern wherein a plurality of electrodes 91 are in contact with a single impregnated zone 16, having a single unimpregnated zone 14 associated therewith. In both FIGS. 28 and 29 welding current flows from upper electrodes 91, across faying surfaces 18 and 22 and through substrate 20 to bottom electrode 91.

FIG. 30 shows a porous body impregnated in a manner identical to that shown in FIG. 28 but wherein the electrode 91 polarity is such that welding current will flow from left electrode 91, through substrate 20 and back through right electrode 91 to form metallurgical bond between faying surfaces 18 and 22.

FIG. 31 shows a porous body 13'''' wherein the unimpregnated zones 14 are in the form of projections. Electrodes 91 are arranged and have a polarity such that metallurgical bonds will form between the faying surface 18, associated with each projecting unimpregnated zone 14, and faying surface 22 associated with substrate 20.

FIG. 32 shows a porous body 13''' impregnated in a manner identical to that shown in FIG. 29 and a rotatable circular electrode 91' for forming a seam weld between porous body 13''' and substrate 20 in accordance with the invention.

It will be clear to those skilled in the art that the use of electrodes in direct contact with the impregnated zone of porous bodies is not necessary to practice the present invention. In fact, an induced electrical current through the porous body and substrate, across the faying surfaces, would serve just as well. The use of electrodes, however, provides a convenient means for causing the welding current to flow as well as introducing the welding pressure of the preferred embodiment.

In a number of welding attempts carried out in accordance with the invention, it was found that the faying surfaces of the porous bodies were somewhat irregular after molding and impregnation. The irregularities could be minimized by grinding the faying surface of the fully impregnated porous body, prior to etching to form the unimpregnated zone.

In many instances, it was also found desirable to "seat" the porous body to the substrate prior to the application of the forge welding current. This was easily carried out by first applying a current density about half as great as the actual welding current density. This initial application of low current density (which was employed with full welding pressure) did not result in a bond but permitted some deformation of the unimpregnated zone so that good contact was obtained between the faying surfaces. It is important to note, however, that the step of "seating" the porous body to the substrate was not a necessary step to carry out the welding method of the invention.

In each of the examples shown herein, the porous bodies were with an electrically conductive material a relatively constant, predetermined distance from the faying surface. A constant distance was only chosen for convenience and the distance from the faying surface can be varied as necessary. Furthermore, the faying surface of the porous body need not be planar in geometry. It is clear that curved and even irregular faying surface can be joined by the method of the invention.

Finally, it will be apparent to those skilled in the art that the method of the present invention can be used to join a porous body to a porous substrate, as well as a substantially solid substrate. While it is believed that the present invention will find the most utility in the joinder of a porous body to a substantially solid substrate, it is only necessary that the substrate have the ability to carry the necessary welding current to permit joinder of the porous body thereto. It is also clear that a porous substrate could be impregnated with an electrically conductive material to enhance its conductance and current carrying ability, all within the scope of the present invention.

The method of the present invention, a method for resistance welding a metallic porous body to a metallic substrate, has been illustrated by various examples. These examples, and the preferred embodiments of the invention disclosed herein, are included for purposes of clarity and illustration and it will be apparent to those skilled in the art that various modifications, alternatives and equivalents of the method of the invention, and apparatus used to practice the same, can be made without departure from the spirit of the invention. Accordingly, the scope of the invention should be defined only by the appended claims and equivalents thereof.

What is claimed is:

1. A method of resistance welding a metallic, porous body to a substrate, said porous body and said substrate each defining a faying surface, said porous body comprising a plurality of components arranged in a three dimensional matrix so as to form interconnecting pores between said components, and a substantial quantity of said components being in electrical communication, said method comprising the steps of:

impregnating said porous body with an electrically conductive material to a predetermined distance from said faying surface defined on said porous body, thereby defining an impregnated zone and an unimpregnated zone, which unimpregnated zone is disposed intermediate said impregnated zone and said faying surface of said porous body;

bringing said faying surfaces of said porous body and said substrate into physical contact; and passing an electrical current through said porous body and substrate, across said faying surfaces, thereby causing metallurgical bonding between said faying surfaces.

2. A method in accordance with claim 1 further comprising the step of forcibly pressing together said porous body and said substrate, said pressing step being carried out during the step of passing said electrical current through said porous body and substrate.

3. A method in accordance with claim 2 wherein the magnitude and duration of said electrical current are controlled to predetermined levels, which levels are sufficient to cause said unimpregnated zone to heat to its hot-working temperature, without melting, and wherein said pressing step is conducted with sufficient force to cause: densification of said unimpregnated zone; metallurgical bonding in the form of forge welding between a substantial number of the components in said unimpregnated zone; and metallurgical bonding in the form of forge welding between the components at the faying surface of the unimpregnated zone of said porous body, and said substrate.

4. A method in accordance with claim 3 wherein the configuration of the components and substrate at the juncture of the faying surfaces present a notched condition which is less severe than the notched condition obtained by conventional sinter bonding said porous body to said substrate.

5. A method in accordance with claim 3 wherein said unimpregnated zone is densified to a condition of substantially zero or zero porosity.

6. A method in accordance with claim 3 wherein said predetermined levels of the duration and magnitude of electrical current are maintained below the levels which cause the electrically conductive material in the impregnated zone from reaching its melting point or solidus temperature.

7. A method in accordance with claim 3 wherein said duration of the application of said electrical current is maintained at a level of less than or equal to about one second.

8. A method in accordance with claim 7 wherein said duration of the application of said electrical current is maintained below a level of about 7/60 of a second.

9. A method in accordance with claim 3 wherein the porosity of said impregnated zone remains substantially unchanged.

10. A method in accordance with claim 3 wherein said porous body and said substrate are fabricated from dissimilar metals or alloys and wherein said metallurgical bonding in the form of forge welding produces no discernable diffusion or alloying zone between said porous body and said substrate.

11. A method in accordance with claim 1 further comprising the step of metallurgically bonding together the components of said porous body, before said impregnating step.

12. A method in accordance with claim 11 wherein said step of metallurgical bonding together said components in said porous body is carried out by electrical resistance heating.

13. A method in accordance with claim 11 wherein said step of metallurgically bonding together said components in said porous body is carried out by sintering said porous body.

14. A method in accordance with claim further comprising simultaneously metallurgically bonding together said components in said porous body and impregnating said porous body by the steps of: immersing said porous body in a molten pool of said electrically conductive impregnating material; maintaining the temperature of said pool and leaving said porous body immersed for a time corresponding to a temperature and time required to carry out said metallurgical bonding of said components by vacuum sintering.

15. A method in accordance with claim 1 wherein said electrically conductive impregnating material is a metal or alloy.

16. A method in accordance with claim 15 wherein said electrically conductive impregnating metal or alloy has a melting point or liquidus temperature lower than the melting point or solidus temperature of the metal or alloy from which the porous body is fabricated and said impregnating step is carried out by immersing said porous body in a molten pool of said electrically conductive impregnating metal or alloy.

17. A method in accordance with claim 15 wherein said porous body is titanium or a titanium based alloy and said electrically conductive impregnating metal or alloy is chosen from the group consisting of calcium, magnesium and base alloys thereof.

18. A method in accordance with claim 1 further comprising the step of removing said impregnating material form said porous body after bonding said faying surfaces.

19. A method in accordance with claim 1 wherein said step of impregnating said porous body with said electrically conductive material to a predetermined distance from the faying surface, is carried out in two steps by: first impregnating said entire porous body with said electrically conductive material; and thereafter removing said electrically conductive material from said porous body to a predetermined distance from the faying surface to form and define said unimpregnated zone.

20. A method in accordance with claim 3 wherein said resistance welding method is carried out with a resistance welding apparatus including electrodes capable of delivering said electrical current to said porous body and capable of carrying out said pressing step, said method further comprising the step of: first seating said porous body and said substrate between said electrodes by causing a first electrical current to pass through said porous body and said substrate during said pressing step but before said step of passing a second electrical current through said porous body and said substrate to form said forge welds, said first electrical current being of a magnitude of about one half the magnitude of said second electrical current.

21. A method of resistance welding a metallic, porous body to a substrate, said porous body and said substrate each defining a faying surface, said porous body comprising a plurality of components arranged in a three dimensional matrix so as to form interconnecting pores between said components, and a substantial quantity of said components being in electrical communication, said method comprising the steps of:

impregnating said porous body with an electrically conductive material to a predetermined distance from said faying surface defined on said porous body, thereby defining an impregnated zone and an unimpregnated zone, which unimpregnated zone is disposed intermediate said impregnated zone and said faying surface of said porous body;

bringing said faying surfaces of said porous body and said solid substrate into physical contact with a third metallic member, said third metallic member being fabricated from a metal or alloy having a composition or base metal different from the metal or alloy from which either the porous body or substrate is fabricated; and passing an electrical current through said porous body, substrate and third metallic member, across said faying surfaces, thereby causing metallurgical bonding between said faying surfaces and said third member.

22. A method in accordance with claim 21 wherein said third metallic member is fabricated in the form of a sheet or foil.

23. A method in accordance with claim 21 further comprising the step of forcibly pressing together said porous body, said substrate and said third metallic member said pressing step being carried out during the step of passing said electrical current through said porous body and substrate.

24. A method in accordance with claim 23 wherein the magnitude and duration of said electrical current are controlled to predetermined levels, which levels are sufficient to cause said unimpregnated zone to heat to its hot-working temperature, without melting, and wherein said pressing step is conducted with sufficient force to cause: densification of said unimpregnated zone; metallurgical bonding in the form of forge welding between a substantial number of the components in said unimpregnated zone; and metallurgical bonding in the form of forge welding between the components at the faying surface of the unimpregnated zone of said porous body and said third metallic member and metallurgical bonding in the form of forge welding between said third metallic member and said substrate.

* * * * *